US007700108B2

(12) United States Patent
Sato et al.

(10) Patent No.: US 7,700,108 B2
(45) Date of Patent: Apr. 20, 2010

(54) TUMOR ANTIGEN PROTEIN AND USE THEREOF

(75) Inventors: Noriyuki Sato, 13-3, Fukuzumi 2-jo 9-chome, Toyohira-ku, Sapporo-shi, Hokkaido (JP); Tomohide Tsukahara, Sapporo (JP); Yuki Nabeta, Sapporo (JP); Satoshi Kawaguchi, Sapporo (JP); Hideyuki Ikeda, Sapporo (JP); Takuro Wada, Sapporo (JP); Toshihiko Yamashita, Sapporo (JP)

(73) Assignees: Dainippon Sumitomo Pharma Co., Ltd., Osaka (JP); Noriyuki Sato, Sapporo (JP)

( * ) Notice: Subject to any disclaimer, the term of this patent is extended or adjusted under 35 U.S.C. 154(b) by 1015 days.

(21) Appl. No.: 10/529,000

(22) PCT Filed: Sep. 19, 2003

(86) PCT No.: PCT/JP03/12037

§ 371 (c)(1),
(2), (4) Date: Mar. 24, 2005

(87) PCT Pub. No.: WO2004/029248

PCT Pub. Date: Apr. 8, 2004

(65) Prior Publication Data

US 2008/0014636 A1    Jan. 17, 2008

(30) Foreign Application Priority Data

Sep. 27, 2002   (JP)   ............... 2002-282345

(51) Int. Cl.
A61K 39/00    (2006.01)
A61K 38/43    (2006.01)
G01N 33/53    (2006.01)

(52) U.S. Cl. ................. 424/185.1; 424/184.1; 435/7.1
(58) Field of Classification Search .................. None
See application file for complete search history.

(56) References Cited

FOREIGN PATENT DOCUMENTS

| EP | 1136555 A1 | 9/2001 |
|----|------------|--------|
| JP | 08-000985 A | 1/1996 |
| JP | 09-122476 A | 5/1997 |
| WO | WO-99/02546 A1 | 1/1999 |
| WO | WO-99/37660 A1 | 7/1999 |
| WO | WO 01/55437 A2 * | 8/2001 |
| WO | WO-01/94629 A2 | 12/2001 |
| WO | WO-02/50103 A2 | 6/2002 |
| WO | WO-03/025136 A2 | 3/2003 |

OTHER PUBLICATIONS

Konya et al, J Gen Virol 1997;78:2615-20.*
May et al, J Gen Virol 1991;72:2989-97.*
Kubo et al, J Immunol 1994;152:3913-24.*
Proc. Natl. Sci. USA,, Dec. 24, 2002 vol. 99, No. 26, pp. 16899-16903, Authors: Strausberg et al.
E. Gilboa et al., Cancer Immunol. Immunother, vol. 46, 1998, pp. 82-87.
M. Nakao et al., Cancer Research, vol. 55, Oct. 1, 1995, pp. 4248-4252.
M. Murakami et al., Cancer Research, vol. 59, Mar. 15, 1999, pp. 1184-1187.
C.L. Slingluff, Jr. et al., Clinical Cancer Research, vol. 7, Oct. 2001, pp. 3012-3024.
S.A. Rosenberg, Immunity, vol. 10, Mar. 1999, pp. 281-287.
H.G. Rammensee et al., Immunogenetics, vol. 41, 1995, pp. 178-228.
M. Herin et al., Int. J. Cancer, vol. 39, 1987, pp. 390-396.
D.D. Kharkevitch et al., Int. J. Cancer, vol. 58, 1994, pp. 317-323.
M. Gotoh et al., Int. J. Cancer, vol. 100, 2002, pp. 565-570.
V.Brichard et al., J. Exp. Med. vol. 178, Aug. 1993, pp. 489-495.
A.B.H. Bakker et al., J. Exp. Med., vol. 179, Mar. 1994, pp. 1005-1009.
B. Fisk et al., J. Exp. Med. vol. 181, Jun. 1995, pp. 2109-2117.
D. Boczkowski et al., J. Exp. Med., vol. 184, Aug. 1996, pp. 465-472.
M.B. Bloom et al., J. Exp. Med., vol. 185, No. 3, Feb. 3, 1997, pp. 453-459.
S. Shichijo et al., J. Exp. Med., vol. 187, No. 3, Feb. 2, 1998, pp. 277-288.
S.A. Rosenberg et al., Journal of the National Cancer Institute, vol. 86, No. 15, Aug. 3, 1994, pp. 1159-1166.
K.Y. Tsang et al., Journal of the National Cancer Institute, vol. 87 No. 13, Jul. 5, 1995, pp. 982-990.
P. Correale et al., Journal of the National Cancer Institute, vol. 89, No. 4, Feb. 19, 1997, pp. 293-300.
W.H. Hildebrand at al., Journal of Immunology. vol. 148, No. 4, Feb. 15, 1992, pp. 1155-1162.
R.T. Kubo et al., Journal of Immunology, vol. 152, 1994, pp. 3913-3924.
L. Rivoltini et al., Journal of Immunology, vol. 154, 1995, pp. 2257-2265.
A. Kondo et al., Journal of Immunology, vol. 155, 1995, pp. 4307-4312.
T. Sudo et al., Journal of Immunology, vol. 155, 1995, pp. 4749-4756.
V. Tsai et al., Journal of Immunology, vol. 158, 1997, pp. 1796-1802.
J. Alexander et al., Journal of Immunology, vol. 159, 1997, pp. 4753-4761.
P. Correale et al., Journal of Immunology, vol. 161, 1998, pp. 3186-3194.
L.H. Butterfield et al., Journal of Immunology, vol. 161, 1998, pp. 5607-5613.
G.Y. Ishioka et al., Journal of Immunology, vol. 162, 1999, pp. 3915-3925.
E.A. Walter et al., New England Journal of Medicine, vol. 333, No. 16, Oct. 19, 1995, pp. 1038-1044.
J.D. Thompson et al., Nucleic Acids Research, vol. 22, No. 22, 1994, pp. 4673-4680.

(Continued)

*Primary Examiner*—Q. Janice Li
(74) *Attorney, Agent, or Firm*—Birch, Stewart, Kolasch & Birch, LLP

(57) ABSTRACT

An inducer of cytotoxic T cells comprising as an active ingredient a protein which comprises the same or substantially the same amino acid sequence as that shown in SEQ ID NO: 2, or a peptide derived from the protein above is provided.

18 Claims, 7 Drawing Sheets

OTHER PUBLICATIONS

Y. Kawakami et al., Proc. Natl. Acad. Sci. USA, vol. 91, Apr. 1994, pp. 3515-3519.
J.D. Altman et al., Science, vol. 274, Oct. 4, 1996, pp. 94-96.
S. Boeckle et al., Virology, vol. 293, 2002, pp. 103-117.
T. Tsukahara et al., Cancer Research, vol. 64, No. 15, Aug. 1, 2004, pp. 5442-5448.
T. Tsukahara et al., "Prognostic Impact and Immunogenicity of a Novel Osteosarcoma Antigen, Papillomavirus Binding Factor, in Patients with Osteosarcoma," Cancer Science, vol. 99, No. 2, Feb. 2008, pp. 368-375.

* cited by examiner

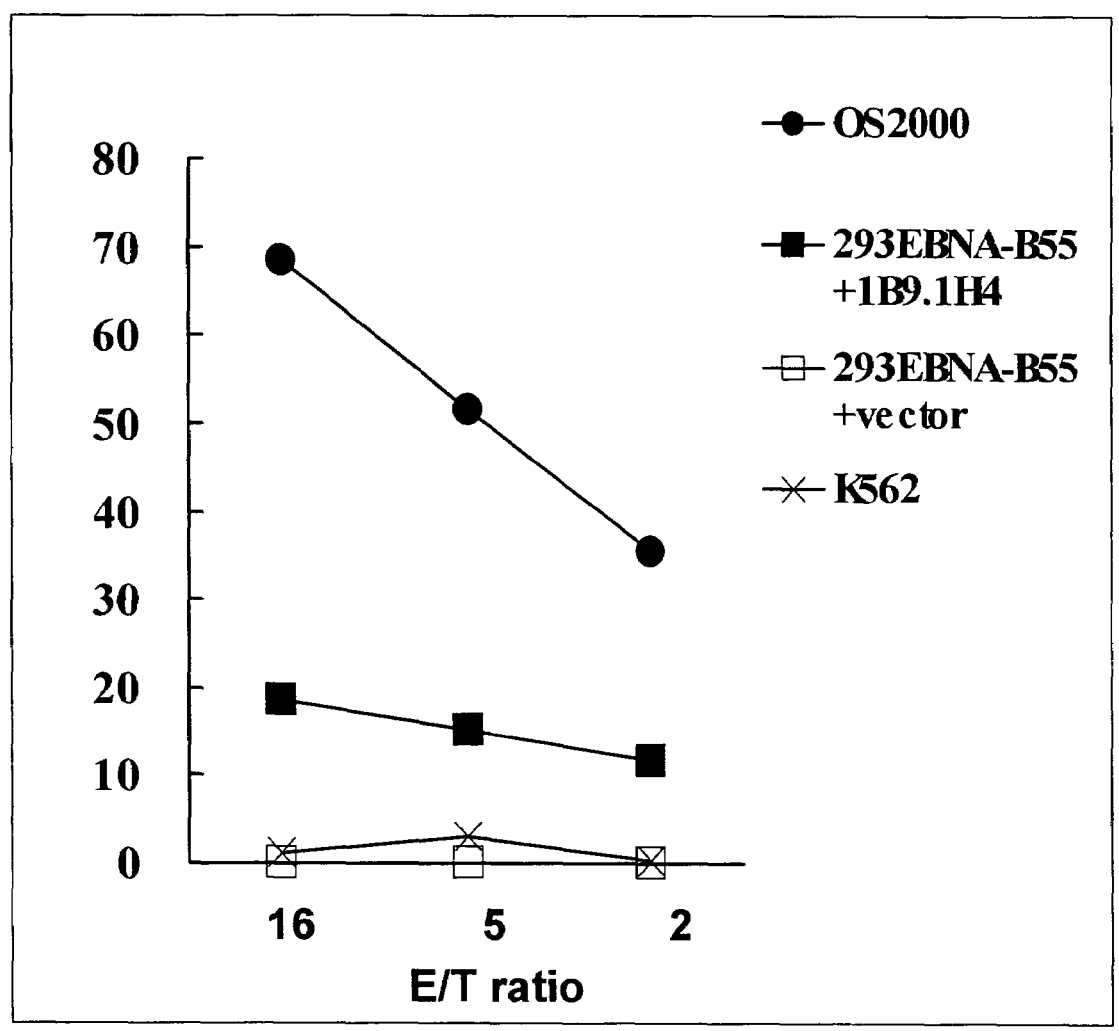

SEQUENCE LISTING

```
<160> NUMBER OF SEQ ID NOS: 55

<210> SEQ ID NO 1
<211> LENGTH: 2068
<212> TYPE: DNA
<213> ORGANISM: Homo sapiens
<220> FEATURE:
<221> NAME/KEY: CDS
<222> LOCATION: (337)..(1878)

<400> SEQUENCE: 1
ctgcacaggg agtttgtctt gtgcaaacaa tttccaaggc agcgttttct tccctgcctg      60
ggagtgcagg gctcagcgcc ttcactttgg aactgactca gagacctaaa gaagcccacc     120
tggccagcgc gaaggggggc cgccgccgcc tcccggtttt gggcagccct ggccagctcc     180
ctgtggcctt ggaggacttc caccgggcag gcgttcccat gatgccaggc taccaggcgc     240
gggggattcc tgcaggccgg cgctgctttt cttagaaccc cctttctaga aaagtacacc     300
tggaggtttt gcttcaaaga gaggagaggc agcagc atg gcg agt gtc ctg tcc      354
                                        Met Ala Ser Val Leu Ser
                                          1               5 cga cgc ctt gga aag cgg tcc ctc ctg gga gcc cgg gtg ttg gga ccc      402
Arg Arg Leu Gly Lys Arg Ser Leu Leu Gly Ala Arg Val Leu Gly Pro
        10                  15                  20 agt gcc tcg gag ggg ccc tcg gct gcc cca ccc tcg gag cca ctg cta      450
Ser Ala Ser Glu Gly Pro Ser Ala Ala Pro Pro Ser Glu Pro Leu Leu
    25                  30                  35 gaa ggg gcc gct ccc cag cct ttc acc acc tct gat gac acc ccc tgc      498
Glu Gly Ala Ala Pro Gln Pro Phe Thr Thr Ser Asp Asp Thr Pro Cys
40                  45                  50 cag gag cag ccc aag gaa gtc ctt aag gct ccc agc acc tcg ggc ctt      546
Gln Glu Gln Pro Lys Glu Val Leu Lys Ala Pro Ser Thr Ser Gly Leu
55                  60                  65                  70 cag cag gtg gcc ttt cag cct ggg cag aag gtt tat gtg tgg tac ggg      594
Gln Gln Val Ala Phe Gln Pro Gly Gln Lys Val Tyr Val Trp Tyr Gly
            75                  80                  85 ggt caa gag tgc aca gga ctg gtg gag cag cac agc tgg atg gag ggt      642
Gly Gln Glu Cys Thr Gly Leu Val Glu Gln His Ser Trp Met Glu Gly
        90                  95                 100 cag gtg acc gtc tgg ctg ctg gag cag aag ctg cag gtc tgc tgc agg      690
Gln Val Thr Val Trp Leu Leu Glu Gln Lys Leu Gln Val Cys Cys Arg
    105                 110                 115 gtg gag gag gtg tgg ctg gca gag ctg cag ggc ccc tgt ccc cag gca      738
```

```
                                                                -continued

Val Glu Glu Val Trp Leu Ala Glu Leu Gln Gly Pro Cys Pro Gln Ala
    120                 125                 130 cca ccc ctg gag ccc gga gcc cag gcc ctg gcc tac agg ccc gtc tcc         786
Pro Pro Leu Glu Pro Gly Ala Gln Ala Leu Ala Tyr Arg Pro Val Ser
135                 140                 145                 150 agg aac atc gat gtc cca aag agg aag tcg gac gca gtg gaa atg gat         834
Arg Asn Ile Asp Val Pro Lys Arg Lys Ser Asp Ala Val Glu Met Asp
                155                 160                 165 gag atg atg gcg gcc atg gtg ctg acg tcc ctg tcc tgc agc cct gtt         882
Glu Met Met Ala Ala Met Val Leu Thr Ser Leu Ser Cys Ser Pro Val
            170                 175                 180 gta cag agt cct ccc ggg acc gag gcc aac ttc tct gct tcc cgt gcg         930
Val Gln Ser Pro Pro Gly Thr Glu Ala Asn Phe Ser Ala Ser Arg Ala
        185                 190                 195 gcc tgc gac cca tgg aag gag agt ggt gac atc tcg gac agc ggc agc         978
Ala Cys Asp Pro Trp Lys Glu Ser Gly Asp Ile Ser Asp Ser Gly Ser
    200                 205                 210 agc act acc agc ggt cac tgg agt ggg agc agt ggt gtc tcc acc ccc        1026
Ser Thr Thr Ser Gly His Trp Ser Gly Ser Ser Gly Val Ser Thr Pro
215                 220                 225                 230 tcg ccc ccc cac ccc cag gcc agc ccc aag tat ttg ggg gat gct ttt        1074
Ser Pro Pro His Pro Gln Ala Ser Pro Lys Tyr Leu Gly Asp Ala Phe
                235                 240                 245 ggt tct ccc caa act gat cat ggc ttt gag acc gat cct gac cct ttc        1122
Gly Ser Pro Gln Thr Asp His Gly Phe Glu Thr Asp Pro Asp Pro Phe
            250                 255                 260 ctg ctg gac gaa cca gct cca cga aaa aga aag aac tct gtg aag gtg        1170
Leu Leu Asp Glu Pro Ala Pro Arg Lys Arg Lys Asn Ser Val Lys Val
        265                 270                 275 atg tac aag tgc ctg tgg cca aac tgt ggc aaa gtt ctg cgc tcc att        1218
Met Tyr Lys Cys Leu Trp Pro Asn Cys Gly Lys Val Leu Arg Ser Ile
    280                 285                 290 gtg ggc atc aaa cga cac gtc aaa gcc ctc cat ctg ggg gac aca gtg        1266
Val Gly Ile Lys Arg His Val Lys Ala Leu His Leu Gly Asp Thr Val
295                 300                 305                 310 gac tct gat cag ttc aag cgg gag gag gat ttc tac tac aca gag gtg        1314
Asp Ser Asp Gln Phe Lys Arg Glu Glu Asp Phe Tyr Tyr Thr Glu Val
                315                 320                 325 cag ctg aag gag gaa tct gct gct gct gct gct gct gcc gca ggc            1362
Gln Leu Lys Glu Glu Ser Ala Ala Ala Ala Ala Ala Ala Ala Gly
            330                 335                 340 acc cca gtc cct ggg act ccc acc tcc gag cca gct ccc acc ccc agc        1410
Thr Pro Val Pro Gly Thr Pro Thr Ser Glu Pro Ala Pro Thr Pro Ser
        345                 350                 355 atg act ggc ctg cct ctg tct gct ctt cca cca cct ctg cac aaa gcc        1458
Met Thr Gly Leu Pro Leu Ser Ala Leu Pro Pro Pro Leu His Lys Ala
    360                 365                 370 cag tcc tcc ggc cca gaa cat cct ggc ccg gag tcc tcc ctg ccc tca        1506
Gln Ser Ser Gly Pro Glu His Pro Gly Pro Glu Ser Ser Leu Pro Ser
375                 380                 385                 390 ggg gct ctc agc aag tca gct cct ggg tcc ttc tgg cac att cag gca        1554
Gly Ala Leu Ser Lys Ser Ala Pro Gly Ser Phe Trp His Ile Gln Ala
                395                 400                 405 gat cat gca tac cag gct ctg cca tcc ttc cag atc cca gtc tca cca        1602
Asp His Ala Tyr Gln Ala Leu Pro Ser Phe Gln Ile Pro Val Ser Pro
            410                 415                 420 cac atc tac acc agt gtc agc tgg gct gct gcc ccc tcc gcc gcc tgc        1650
His Ile Tyr Thr Ser Val Ser Trp Ala Ala Ala Pro Ser Ala Ala Cys
        425                 430                 435
```

```
tct ctc tct ccg gtc cgg agc cgg tcg cta agc ttc agc gag ccc cag    1698
Ser Leu Ser Pro Val Arg Ser Arg Ser Leu Ser Phe Ser Glu Pro Gln
        440                 445                 450 cag cca gca cct gcg atg aaa tct cat ctg atc gtc act tct cca ccc    1746
Gln Pro Ala Pro Ala Met Lys Ser His Leu Ile Val Thr Ser Pro Pro
455                 460                 465                 470 cgg gcc cag agt ggt gcc agg aaa gcc cga ggg gag gct aag aag tgc    1794
Arg Ala Gln Ser Gly Ala Arg Lys Ala Arg Gly Glu Ala Lys Lys Cys
                475                 480                 485 cgc aag gtg tat ggc atc gag cac cgg gac cag tgg tgc acg gcg tgc    1842
Arg Lys Val Tyr Gly Ile Glu His Arg Asp Gln Trp Cys Thr Ala Cys
                490                 495                 500 cgg tgg aag aag gcc tgc cag cgc ttt ctg gac tga gctgtgctgc         1888
Arg Trp Lys Lys Ala Cys Gln Arg Phe Leu Asp
        505                 510 aggttctact ctgttcctgg ccctgccggc agccactgac aagaggccag tgtgtcacca    1948
gccctcagca gaaaccgaaa gagaaagaac ggaaacacgg agtttgggct ctgttggcta    2008
aggtgtaaca cttaaagcaa ttttctccca ttgtgcgaac attttatttt ttaaaaaaaa    2068

<210> SEQ ID NO 2
<211> LENGTH: 513
<212> TYPE: PRT
<213> ORGANISM: Homo sapiens

<400> SEQUENCE: 2

Met Ala Ser Val Leu Ser Arg Arg Leu Gly Lys Arg Ser Leu Leu Gly
 1               5                  10                  15

Ala Arg Val Leu Gly Pro Ser Ala Ser Glu Gly Pro Ser Ala Ala Pro
            20                  25                  30

Pro Ser Glu Pro Leu Leu Glu Gly Ala Ala Pro Gln Pro Phe Thr Thr
        35                  40                  45

Ser Asp Asp Thr Pro Cys Gln Glu Gln Pro Lys Glu Val Leu Lys Ala
    50                  55                  60

Pro Ser Thr Ser Gly Leu Gln Gln Val Ala Phe Gln Pro Gly Gln Lys
65                  70                  75                  80

Val Tyr Val Trp Tyr Gly Gly Gln Glu Cys Thr Gly Leu Val Glu Gln
                85                  90                  95

His Ser Trp Met Glu Gly Gln Val Thr Val Trp Leu Leu Glu Gln Lys
            100                 105                 110

Leu Gln Val Cys Cys Arg Val Glu Glu Val Trp Leu Ala Glu Leu Gln
        115                 120                 125

Gly Pro Cys Pro Gln Ala Pro Pro Leu Glu Pro Gly Ala Gln Ala Leu
    130                 135                 140

Ala Tyr Arg Pro Val Ser Arg Asn Ile Asp Val Pro Lys Arg Lys Ser
145                 150                 155                 160

Asp Ala Val Glu Met Asp Glu Met Met Ala Ala Met Val Leu Thr Ser
                165                 170                 175

Leu Ser Cys Ser Pro Val Val Gln Ser Pro Gly Thr Glu Ala Asn
        180                 185                 190

Phe Ser Ala Ser Arg Ala Ala Cys Asp Pro Trp Lys Glu Ser Gly Asp
    195                 200                 205

Ile Ser Asp Ser Gly Ser Thr Thr Ser Gly His Trp Ser Gly Ser
    210                 215                 220

Ser Gly Val Ser Thr Pro Ser Pro Pro His Pro Gln Ala Ser Pro Lys
225                 230                 235                 240
```

-continued

```
Tyr Leu Gly Asp Ala Phe Gly Ser Pro Gln Thr Asp His Gly Phe Glu
                245                 250                 255

Thr Asp Pro Asp Pro Phe Leu Leu Asp Glu Pro Ala Pro Arg Lys Arg
            260                 265                 270

Lys Asn Ser Val Lys Val Met Tyr Lys Cys Leu Trp Pro Asn Cys Gly
        275                 280                 285

Lys Val Leu Arg Ser Ile Val Gly Ile Lys Arg His Val Lys Ala Leu
    290                 295                 300

His Leu Gly Asp Thr Val Asp Ser Asp Gln Phe Lys Arg Glu Glu Asp
305                 310                 315                 320

Phe Tyr Tyr Thr Glu Val Gln Leu Lys Glu Glu Ser Ala Ala Ala Ala
                325                 330                 335

Ala Ala Ala Ala Ala Gly Thr Pro Val Pro Gly Thr Pro Thr Ser Glu
            340                 345                 350

Pro Ala Pro Thr Pro Ser Met Thr Gly Leu Pro Leu Ser Ala Leu Pro
        355                 360                 365

Pro Pro Leu His Lys Ala Gln Ser Ser Gly Pro Glu His Pro Gly Pro
    370                 375                 380

Glu Ser Ser Leu Pro Ser Gly Ala Leu Ser Lys Ser Ala Pro Gly Ser
385                 390                 395                 400

Phe Trp His Ile Gln Ala Asp His Ala Tyr Gln Ala Leu Pro Ser Phe
                405                 410                 415

Gln Ile Pro Val Ser Pro His Ile Tyr Thr Ser Val Ser Trp Ala Ala
            420                 425                 430

Ala Pro Ser Ala Ala Cys Ser Leu Ser Pro Val Arg Ser Arg Ser Leu
        435                 440                 445

Ser Phe Ser Glu Pro Gln Gln Pro Ala Pro Ala Met Lys Ser His Leu
    450                 455                 460

Ile Val Thr Ser Pro Pro Arg Ala Gln Ser Gly Ala Arg Lys Ala Arg
465                 470                 475                 480

Gly Glu Ala Lys Lys Cys Arg Lys Val Tyr Gly Ile Glu His Arg Asp
                485                 490                 495

Gln Trp Cys Thr Ala Cys Arg Trp Lys Lys Ala Cys Gln Arg Phe Leu
            500                 505                 510

Asp
```

<210> SEQ ID NO 3
<211> LENGTH: 1901
<212> TYPE: DNA
<213> ORGANISM: Homo sapiens
<220> FEATURE:
<221> NAME/KEY: misc_feature
<222> LOCATION: (1191)..(1191)
<223> OTHER INFORMATION: n is a, c, g, or t

<400> SEQUENCE: 3

```
ggctggcaga gctgcagggc ccctgtcccc aggcaccacc cctggagccc ggagcccagg      60
ccctggccta caggcccgtc tccaggaaca tcgatgtccc aaagaggaag tcggacgcag     120
tggaaatgga tgagatgatg gcggccatgg tgctgacgtc cctgtcctgc agccctgttg     180
tacagagtcc tcccgggacc gaggccaact tctctgcttc ccgtgcggcc tgcgacccat     240
ggaaggagag tggtgacatc tcggacagcg gcagcagcac taccagcggt cactggagtg     300
ggagcagtgg tgtctccacc ccctcgcccc ccacccccca ggccagcccc aagtatttgg     360
gggatgcttt tggttctccc caaactgatc atggctttga gaccgatcct gacccttttcc    420
```

```
tgctggacga accagctcca cgaaaaagaa agaactctgt gaaggtgatg tacaagtgcc      480
tgtggccaaa ctgtggcaaa gttctgcgct ccattgtggg catcaaacga cacgtcaaag      540
ccctccatct gggggacaca gtggactctg atcagttcaa gcgggaggag gatttctact      600
acacagaggt gcagctgaag gaggaatctg ctgctgctgc tgctgctgct gccgcaggca      660
ccccagtccc tgggactccc acctccgagc cagctccac ccccagcatg actggcctgc      720
ctctgtctgc tcttccacca cctctgcaca agcccagtc ctccggccca gaacatcctg      780
gcccggagtc ctccctgccc tcaggggctc tcagcaagtc agctcctggg tccttctggc      840
acattcaggc agatcatgca taccaggctc tgccatcctt ccagatccca gtctcaccac      900
acatctacac cagtgtcagc tgggctgctg cccctccgc cgcctgctct ctctctccgg      960
tccggagccg gtcgctaagc ttcagcgagc cccagcagcc agcacctgcg atgaaatctc     1020
atctgatcgt cacttctcca ccccgggccc agagtggtgc caggtgagat gtccgctgtc     1080
gtcccctgcc ttctggtttc tgtgccctgt ctccagtggc gtggactccg accccaccca     1140
gatgaagtca ccagggttag tccccagaga ggagcccaga tggcggatgc nccagatggg     1200
atgactgttt ggtcctcaga gcctctggcc cctggtcctg gtgactttg ccgggagctg     1260 ccccttggc ctctgcttgt tcccagcc ccacttggcc actctcctgg gcccaccacc     1320 tgtgtgggc tcgatttgca ttcctctctt tctgcaggaa agcccgaggg gaggctaaga     1380
agtgccgcaa ggtgtatggc atcgagcacc gggaccagtg gtgcacggcg tgccggtgga     1440
agaaggcctg ccagcgcttt ctggactgag ctgtgctgca ggttctactc tgttcctggc     1500
cctgccggca gccactgaca agaggccagt gtgtcaccag ccctcagcag aaaccgaaag     1560
agaaagaacg gaaacacgga gtttgggctc tgttggctaa ggtgtaacac ttaaagcaat     1620
tttctcccat tgtgcgaaca ttttattttt taaaaaaag aaacaaaaat attttccccc     1680
ctaaaatagg agagagccaa aactgaccaa ggctattcag cagtgaacca gtgaccaaag     1740
aattaattac cctccgtttc ccacatcccc actctctagg ggattagctt gtgcgtgtca     1800
aaagaaggaa cagctcgttc tgcttcctgc tgagtcggtg aattctttgc tttctaaact     1860
cttccagaaa ggactgtgag caagatgaat ttacttttct t                        1901
```

<210> SEQ ID NO 4
<211> LENGTH: 33
<212> TYPE: DNA
<213> ORGANISM: Artificial Sequence
<220> FEATURE:
<223> OTHER INFORMATION: PCR primer used to amplify PBF cDNA

<400> SEQUENCE: 4

```
tactagctag ctaaggcagc agcatggcga gtg                                   33
```

<210> SEQ ID NO 5
<211> LENGTH: 34
<212> TYPE: DNA
<213> ORGANISM: Artificial Sequence
<220> FEATURE:
<223> OTHER INFORMATION: PCR primer used to amplify PBF cDNA

<400> SEQUENCE: 5

```
aaatatgcgg ccgcggccag gaacagagta gaac                                  34
```

<210> SEQ ID NO 6
<211> LENGTH: 9
<212> TYPE: PRT
<213> ORGANISM: Artificial Sequence

```
<220> FEATURE:
<223> OTHER INFORMATION: Synthetic peptide derived from SEQ ID NO: 2
      that can be recognized by CTLs when bound to HLA-A24 antigen

<400> SEQUENCE: 6

Ala Tyr Arg Pro Val Ser Arg Asn Ile
 1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 7

Asp Phe Tyr Tyr Thr Glu Val Gln Leu
 1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 8

Gly Phe Glu Thr Asp Pro Asp Pro Phe
 1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 9

Lys Tyr Leu Gly Asp Ala Phe Gly Ser
 1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 10

Arg Ser Leu Leu Gly Ala Arg Val Leu
 1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 11

Ala Ala Pro Pro Ser Glu Pro Leu Leu
 1               5
```

```
<210> SEQ ID NO 12
<211> LENGTH: 9
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 12

Ile Tyr Thr Ser Val Ser Trp Ala Ala
 1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 13

Thr Val Trp Leu Leu Glu Gln Lys Leu
 1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 14

His Pro Gln Ala Ser Pro Lys Tyr Leu
 1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 15

Leu Ser Pro Val Arg Ser Arg Ser Leu
 1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 16

Met Tyr Lys Cys Leu Trp Pro Asn Cys
 1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen
```

-continued

```
<400> SEQUENCE: 17

Leu Trp Pro Asn Cys Gly Lys Val Leu
 1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 18

Cys Gln Glu Gln Pro Lys Glu Val Leu
 1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 19

Ala Ala Pro Ser Ala Ala Cys Ser Leu
 1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 20

Glu Gly Gln Val Thr Val Trp Leu Leu
 1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 21

Met Ala Ala Met Val Leu Thr Ser Leu
 1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 22

Gly Pro Cys Pro Gln Ala Pro Pro Leu
 1               5

<210> SEQ ID NO 23
<211> LENGTH: 9
<212> TYPE: PRT
```

```
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 23

Ala Pro Thr Pro Ser Met Thr Gly Leu
 1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 24

Arg Trp Lys Lys Ala Cys Gln Arg Phe
 1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 25

Ser Ala Ala Pro Pro Ser Glu Pro Leu
 1               5

<210> SEQ ID NO 26
<211> LENGTH: 10
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 26

Trp Tyr Gly Gly Gln Glu Cys Thr Gly Leu
 1               5                   10

<210> SEQ ID NO 27
<211> LENGTH: 10
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 27

Ala Tyr Gln Ala Leu Pro Ser Phe Gln Ile
 1               5                   10

<210> SEQ ID NO 28
<211> LENGTH: 10
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 28

Gly Phe Glu Thr Asp Pro Asp Pro Phe Leu
 1               5                   10
```

```
<210> SEQ ID NO 29
<211> LENGTH: 10
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 29

Arg Val Glu Glu Val Trp Leu Ala Glu Leu
  1               5                  10

<210> SEQ ID NO 30
<211> LENGTH: 10
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 30

Ser Phe Gln Ile Pro Val Ser Pro His Ile
  1               5                  10

<210> SEQ ID NO 31
<211> LENGTH: 10
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 31

Val Tyr Val Trp Tyr Gly Gly Gln Glu Cys
  1               5                  10

<210> SEQ ID NO 32
<211> LENGTH: 10
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 32

Val Thr Val Trp Leu Leu Glu Gln Lys Leu
  1               5                  10

<210> SEQ ID NO 33
<211> LENGTH: 10
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 33

Trp Met Glu Gly Gln Val Thr Val Trp Leu
  1               5                  10

<210> SEQ ID NO 34
<211> LENGTH: 10
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen
```

```
<400> SEQUENCE: 34

Arg Trp Lys Lys Ala Cys Gln Arg Phe Leu
 1               5                  10

<210> SEQ ID NO 35
<211> LENGTH: 10
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 35

Leu Pro Leu Ser Ala Leu Pro Pro Pro Leu
 1               5                  10

<210> SEQ ID NO 36
<211> LENGTH: 10
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 36

Val Gly Ile Lys Arg His Val Lys Ala Leu
 1               5                  10

<210> SEQ ID NO 37
<211> LENGTH: 10
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 37

Asn Ser Val Lys Val Met Tyr Lys Cys Leu
 1               5                  10

<210> SEQ ID NO 38
<211> LENGTH: 10
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 38

Gln Gly Pro Cys Pro Gln Ala Pro Pro Leu
 1               5                  10

<210> SEQ ID NO 39
<211> LENGTH: 10
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 39

Ile Gln Ala Asp His Ala Tyr Gln Ala Leu
 1               5                  10

<210> SEQ ID NO 40
<211> LENGTH: 10
```

```
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 40

Met Met Ala Ala Met Val Leu Thr Ser Leu
 1               5                  10

<210> SEQ ID NO 41
<211> LENGTH: 10
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 41

Ile Tyr Thr Ser Val Ser Trp Ala Ala Ala
 1               5                  10

<210> SEQ ID NO 42
<211> LENGTH: 10
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 42

Val Tyr Gly Ile Glu His Arg Asp Gln Trp
 1               5                  10

<210> SEQ ID NO 43
<211> LENGTH: 10
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 43

Ser Leu Ser Pro Val Arg Ser Arg Ser Leu
 1               5                  10

<210> SEQ ID NO 44
<211> LENGTH: 10
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 44

Ala Ala Ala Pro Ser Ala Ala Cys Ser Leu
 1               5                  10

<210> SEQ ID NO 45
<211> LENGTH: 10
<212> TYPE: PRT
<213> ORGANISM: Artificial Sequence
<220> FEATURE:
<223> OTHER INFORMATION: Synthetic peptide derived from SEQ ID NO: 2
      that can be recognized by CTLs when bound to HLA-A24 antigen

<400> SEQUENCE: 45

Gln Pro Ala Pro Ala Met Lys Ser His Leu
```

-continued

```
            1               5                  10
```

<210> SEQ ID NO 46
<211> LENGTH: 12
<212> TYPE: PRT
<213> ORGANISM: Artificial Sequence
<220> FEATURE:
<223> OTHER INFORMATION: HLA-B55-restricted tumor antigen peptide

<400> SEQUENCE: 46

```
Cys Thr Ala Cys Arg Trp Lys Lys Ala Cys Gln Arg
  1               5                  10
```

<210> SEQ ID NO 47
<211> LENGTH: 9
<212> TYPE: PRT
<213> ORGANISM: Artificial Sequence
<220> FEATURE:
<223> OTHER INFORMATION: A synthetic peptide that can be recognized by
      CTLs when bound to HLA-B55 antigen

<400> SEQUENCE: 47

```
Cys Thr Ala Cys Arg Trp Lys Lys Ala
  1               5
```

<210> SEQ ID NO 48
<211> LENGTH: 9
<212> TYPE: PRT
<213> ORGANISM: Artificial Sequence
<220> FEATURE:
<223> OTHER INFORMATION: A synthetic peptide that can be recognized by
      CTLs when bound to HLA-B55 antigen

<400> SEQUENCE: 48

```
Thr Ala Cys Arg Trp Lys Lys Ala Cys
  1               5
```

<210> SEQ ID NO 49
<211> LENGTH: 9
<212> TYPE: PRT
<213> ORGANISM: Artificial Sequence
<220> FEATURE:
<223> OTHER INFORMATION: A synthetic peptide that can be recognized by
      CTLs when bound to HLA-B55 antigen

<400> SEQUENCE: 49

```
Ala Cys Arg Trp Lys Lys Ala Cys Gln
  1               5
```

<210> SEQ ID NO 50
<211> LENGTH: 9
<212> TYPE: PRT
<213> ORGANISM: Artificial Sequence
<220> FEATURE:
<223> OTHER INFORMATION: A synthetic peptide that can be recognized by
      CTLs when bound to HLA-B55 antigen

<400> SEQUENCE: 50

```
Cys Arg Trp Lys Lys Ala Cys Gln Arg
  1               5
```

<210> SEQ ID NO 51
<211> LENGTH: 10
<212> TYPE: PRT
<213> ORGANISM: Artificial Sequence
<220> FEATURE:
<223> OTHER INFORMATION: A synthetic peptide that can be recognized by
      CTLs when bound to HLA-B55 antigen

```
<400> SEQUENCE: 51

Cys Thr Ala Cys Arg Trp Lys Lys Ala Cys
1               5                   10

<210> SEQ ID NO 52
<211> LENGTH: 10
<212> TYPE: PRT
<213> ORGANISM: Artificial Sequence
<220> FEATURE:
<223> OTHER INFORMATION: A synthetic peptide that can be recognized by
      CTLs when bound to HLA-B55 antigen

<400> SEQUENCE: 52

Thr Ala Cys Arg Trp Lys Lys Ala Cys Gln
1               5                   10

<210> SEQ ID NO 53
<211> LENGTH: 10
<212> TYPE: PRT
<213> ORGANISM: Artificial Sequence
<220> FEATURE:
<223> OTHER INFORMATION: A synthetic peptide that can be recognized by
      CTLs when bound to HLA-B55 antigen

<400> SEQUENCE: 53

Ala Cys Arg Trp Lys Lys Ala Cys Gln Arg
1               5                   10

<210> SEQ ID NO 54
<211> LENGTH: 11
<212> TYPE: PRT
<213> ORGANISM: Artificial Sequence
<220> FEATURE:
<223> OTHER INFORMATION: A synthetic peptide that can be recognized by
      CTLs when bound to HLA-B55 antigen

<400> SEQUENCE: 54

Cys Thr Ala Cys Arg Trp Lys Lys Ala Cys Gln
1               5                   10

<210> SEQ ID NO 55
<211> LENGTH: 11
<212> TYPE: PRT
<213> ORGANISM: Artificial Sequence
<220> FEATURE:
<223> OTHER INFORMATION: A synthetic peptide that can be recognized by
      CTLs when bound to HLA-B55 antigen

<400> SEQUENCE: 55

Thr Ala Cys Arg Trp Lys Lys Ala Cys Gln Arg
1               5                   10
```

TUMOR ANTIGEN PROTEIN AND USE THEREOF

TECHNICAL FIELD

The present invention relates to a tumor antigen protein. More particularly, the present invention relates to use of a tumor antigen protein PBF and a gene encoding the same in the field of cancer immunology.

BACKGROUND ART

It is known that the cell mediated immunity, particularly a cytotoxic T cell (hereinafter, referred to as "CTL") plays a significant role in vivo rejection of tumor cells or viral infection cells. CTLs recognize a complex between a tumor antigen peptide and a major histocompatibility complex class I antigen, i.e., MHC class I antigen, which is referred to as "HLA antigen" in the case of human, on the cell surface of tumor cells, and attack and kill the cells.

Tumor antigen peptides are generated through the intracellular processing of intracellularly synthesized proteins specific for tumors (tumor antigen proteins) and degradated by proteases. The resultant tumor antigen peptides form a complex with MHC class I antigens (HLA antigens) in endoplasmic reticulum and transported to the cell surface where said complex is presented as an antigen. CTLs, when recognize the complex presented as an antigen, exhibit the anti-tumor effects through cytotoxic action or production of lymphokines. As a consequence of elucidation of a series of such actions, a therapy of tumor patients has become available, wherein a tumor antigen protein or peptide is administered as an immunotherapeutic agent, i.e., cancer vaccine, thereby enhancing tumor-specific CTLs in the patient.

Typical examples of tumor antigen proteins include those described in *Immunity*, 10: 281, 1999, Table 1. Specific examples include melanosome antigens such as melanocyte tissue specific proteins, for instance, gp100 (*J. Exp. Med.*, 179:1005, 1994), MART-1 (*Proc. Natl. Acad. Sci. USA*, 91:3515, 1994) and melanosome proteins such as tyrosinase (*J. Exp. Med.*, 178:489, 1993). Examples of tumor antigen proteins other than melanoma include HER2/neu (*J. Exp. Med.*, 181: 2109, 1995), CEA (*J. Natl. Cancer. Inst.*, 87: 982, 1995), and PSA (*J. Natl. Cancer. Inst.*, 89: 293, 1997), etc. However, tumor antigen proteins broadly applicable to cancers (tumors) including sarcomas such as osteosarcoma have not been reported yet.

Papillomavirus binding factor (PBF, GenBank data base Accession No. AF263928) has been identified as a factor recognizing the E2 binding site of papillomavirus (*Virology* 293, 103-117, 2002). However, nothing has been known about the relationships between the PBF and tumors.

DISCLOSURE OF INVENTION

A purpose of the present invention is to provide use of a tumor antigen protein PBF and a gene encoding the same in the field of cancer immunology.

The present inventors have established osteosarcoma cell line OS2000 from a patient of osteosarcoma and then a CTL cell line TcOS2000cl-303 having cytotoxic activity against the OS2000 cells.

The inventors then prepared 293-EBNA-B55 and 293-EBNA-A24 cells for assay by introducing into 293-EBNA cell lines the HLA-B5502 gene (one of HLA-B55) and the HLA-A2402 gene (one of HLA-A24), respectively. The 293-EBNA-B55 or 293-EBNA-A24 cells were transformed with a cDNA clone pool of cDNA library prepared from OS2000, and the resultant transfectants were treated with TcOS2000cl-303. The amount of LDH resulting from the cytotoxic effect of TcOS2000cl-303 was measured to determine whether or not TcOS2000cl-303 reacted. After repeating an enormous number of screenings, the present inventors have finally found that papillomavirus binding factor (PBF, GenBank Accession No. AF263928) is a novel tumor antigen protein having CTL inducing activity. The nucleotide and amino acid sequences of PBF are shown in SEQ ID NO: 1 and 2, respectively. The fact that PBF serves as a tumor antigen protein has neither known nor expected so far and is quite a novel finding.

The present inventors then confirmed that PBF comprises a tumor antigen peptide region(s) capable of binding to an HLA antigen. The inventors also found that the PBF is extensively and highly expressed in sarcomas and renal cancer.

The tumor antigen protein PBF, tumor antigen peptides derived therefrom, or genes encoding the same can be used in vivo or in vitro as an inducer of CTL or a cancer vaccine, wherein they exert therapeutic or ameliorative effects on tumors such as oseteosarcomas, renal cancer, and the like. PBF is also useful as a marker for tumors such as sarcomas, renal cancer, and the like.

The present invention has been established on the basis of the findings above.

Thus, the present invention encompasses the followings.

(1) An inducer of CTL comprising as an active ingredient a protein which comprises the same or substantially the same amino acid sequence as that shown in SEQ ID NO: 2.

(2) The inducer of CTL of (1), wherein the protein which comprises the same or substantially the same amino acid sequence as that shown in SEQ ID NO: 2 is selected from (a) to (d) below:

(a) a protein comprising the amino acid sequence of SEQ ID NO: 2;

(b) a protein comprising an amino acid sequence wherein one or more amino acids are deleted, substituted and/or added in the amino acid sequence shown in SEQ ID NO: 2, and being characterized by that a cells expressing the protein is recognized by CTLs;

(c) a protein comprising an amino acid sequence having at least 70% sequence identity with the amino acid sequence shown in SEQ ID NO: 2, and being characterized by that a cell expressing the protein is recognized by CTLs; and (d) a protein being encoded by a polynucleotide capable of hybridizing to a complementary strand of polynucleotide encoding the amino acid sequence shown in SEQ ID NO: 2 under stringent conditions, and being characterized by that a cell expressing the protein is recognized by CTLs.

(3) A partial peptide of a protein comprising the same or substantially the same amino acid sequence as that shown in SEQ ID NO: 2, which peptide is recognized by CTLs when bound to an HLA antigen.

(4) The peptide of (3), wherein the protein comprising the same or substantially the same amino acid sequence as that shown in SEQ ID NO: 2 is selected from (a) to (d) below:

(a) a protein comprising the amino acid sequence of SEQ ID NO: 2;

(b) a protein comprising an ammo acid sequence wherein one or more amino acids are deleted, substituted and/or added in the amino acid sequence shown in SEQ ID NO: 2, and being characterized by that a cell expressing the protein is recognized by CTLs;

(c) a protein comprising an amino acid sequence having at least 70% sequence identity with the amino acid sequence shown in SEQ ID NO: 2, and being characterized by that a cell expressing the protein is recognized by CTLs; and (d) a protein being encoded by a polynucleotide capable of hybridizing to a complementary strand of polynucleotide encoding the amino acid sequence shown in SEQ ID NO: 2 under stringent conditions, and being characterized by that a cell expressing the protein is recognized by CTLs.

(5) The peptide of (3) or (4), wherein the HLA antigen is HLA-A24 or HLA-B55.

(6) The peptide of (5), which comprises an amino acid sequence shown in any one of SEQ ID NO: 6-55.

(7) The peptide of (5), which comprises an amino acid sequence wherein, in the sequence shown in any one of SEQ ID NO: 6-45, the amino acid residue at position 2 is substituted by tyrosine, phenylalanine, methionine or tryptophan, and/or the C terminal amino acid by phenylalanine, leucine, isoleucine, tryptophan or methionine.

(8) An epitopic peptide comprising a peptide of any one of (3) to (7).

(9) An inducer of CTL comprising a peptide of any one of (3) to (8) as an active ingredient.

(10) An inducer of CTL comprising a polynucleotide encoding a protein comprising the same or substantially the same amino acid sequence as that shown in SEQ ID NO: 2.

(11) The inducer of CTL of (10), wherein the polynucleotide encoding a protein comprising the same or substantially the same amino acid sequence as that shown in SEQ ID NO: 2 is selected from (a) to (g) below:

(a) a polynucleotide comprising the base sequence shown in SEQ ID NO: 1;

(b) a polynucleotide comprising the base sequence at positions 337-1878 of that shown in SEQ ID NO: 1;

(c) a polynucleotide comprising a base sequence encoding the amino acid sequence of SEQ ID NO: 2;

(d) a polynucleotide comprising the base sequence shown in SEQ ID NO: 3;

(e) a polynucleotide capable of hybridizing to a complementary strand of any one of polynucleotides (a) to (d) above under stringent conditions, and being characterized by that a cell expressing a protein encoded by the polynucleotide is recognized by CTLs;

(f) a polynucleotide comprising a base sequence having at least 70% sequence identity with a polynucleotide set forth in any one of (a) to (d) above, and being characterized by that a cell expressing a protein encoded by the polynucleotide is recognized by CTLs; and (g) a polynucleotide encoding a protein comprising an amino acid sequence, wherein one or more amino acids are deleted, substituted and/or added in the amino acid sequence encoded by any one of polynucleotides (a) to (d) above, and being characterized by that a cell expressing the protein encoded by the polynucleotide is recognized by CTLs.

(12) The inducer of CTL of (10) or (11), wherein the polynucleotide comprises a base sequence selected from those shown in SEQ ID NO: 1, position 337-1878 of SEQ ID NO: 1 or SEQ ID NO: 3.

(13) A nucleic acid comprising a polynucleotide encoding a peptide set forth in any one of (3) to (8).

(14) An inducer of CTL comprising the nucleic acid of (13).

(15) A method for producing an antigen-presenting cell comprising the step of bringing a cell having antigen-presenting ability into contact with any one of following (a) to (d) in nitro:

(a) a protein comprising the same or substantially the same amino acid sequence as that shown in SEQ ID NO: 2;

(b) a nucleic acid comprising a polynucleotide encoding the protein of (a);

(c) a peptide set forth in any one of (3) to (8); and (d) a nucleic acid comprising a polynucleotide encoding the peptide of (c).

(16) An antigen-presenting cell obtainable according to the method of (15).

(17) A method for inducing a CTL comprising the step of bringing peripheral lymphocyte cells into contact with any one of following (a) to (d) in vitro:

(a) a protein comprising the same or substantially the same amino acid sequence as that shown in SEQ ID NO: 2;

(b) a nucleic acid comprising a polynucleotide encoding the protein of (a);

(c) a peptide set forth in any one of (3) to (8); and (d) a nucleic acid comprising a polynucleotide encoding the peptide of (c).

(18) The CTL inducible by the method of (17).

(19) An antibody which specifically binds to the polypeptide set forth in any one of (3) to (7).

(20) A tumor marker comprising a polynucleotide and/or a complementary polynucleotide thereof, which polynucleotide comprises at least 15 contiguous nucleotides in the base sequence of a polynucleotide encoding a protein comprising the same or substantially the same amino acid sequence as that shown in SEQ ID NO: 2.

(21) The tumor marker of (20), which is a polynucleotide and/or a complementary polynucleotide thereof, which polynucleotide comprises at least 15 contiguous nucleotides in the base sequence of SEQ ID NO 1 or SEQ ID NO: 3.

(22) A tumor marker comprising at least 8 contiguous amino acids in the amino acid sequence of a protein comprising the same or substantially the same amino acid sequence as that shown in SEQ ID NO: 2.

(23) The tumor marker of (22), which comprises at least 8 contiguous amino acids in the amino acid sequence shown in SEQ ID NO: 2.

(24) A tumor marker comprising an antibody to a protein comprising the same or substantially the same amino acid sequence as that shown in SEQ ID NO:2, or the antibody set forth in (19).

(25) The tumor marker of (24) comprising an antibody to the protein comprising the amino acid sequence shown in SEQ ID NO:2.

26) An HLA tetramer comprising a peptide set forth in any one of (3) to (7) and an HLA antigen.

(27) A tumor marker comprising the tetramer of (26).

(28) The tumor marker set forth in any one of (20) to (25), and (27), wherein the tumor is sarcoma or renal cancer.

(29) A diagnostic agent for tumor comprising a tumor marker set forth in any one of (20)-(25), (27) and (28).

(30) The inducer of CTL set forth in (1), (2), (9), (10), (11), (12) or (14), which is used as a cancer vaccine.

EBNA-A24 and 293-EBNA-B55 cells, respectively. In the figure, the abscissa axis represents E/T ratio and the ordinate axis cytotoxic activity.

Figure 3:
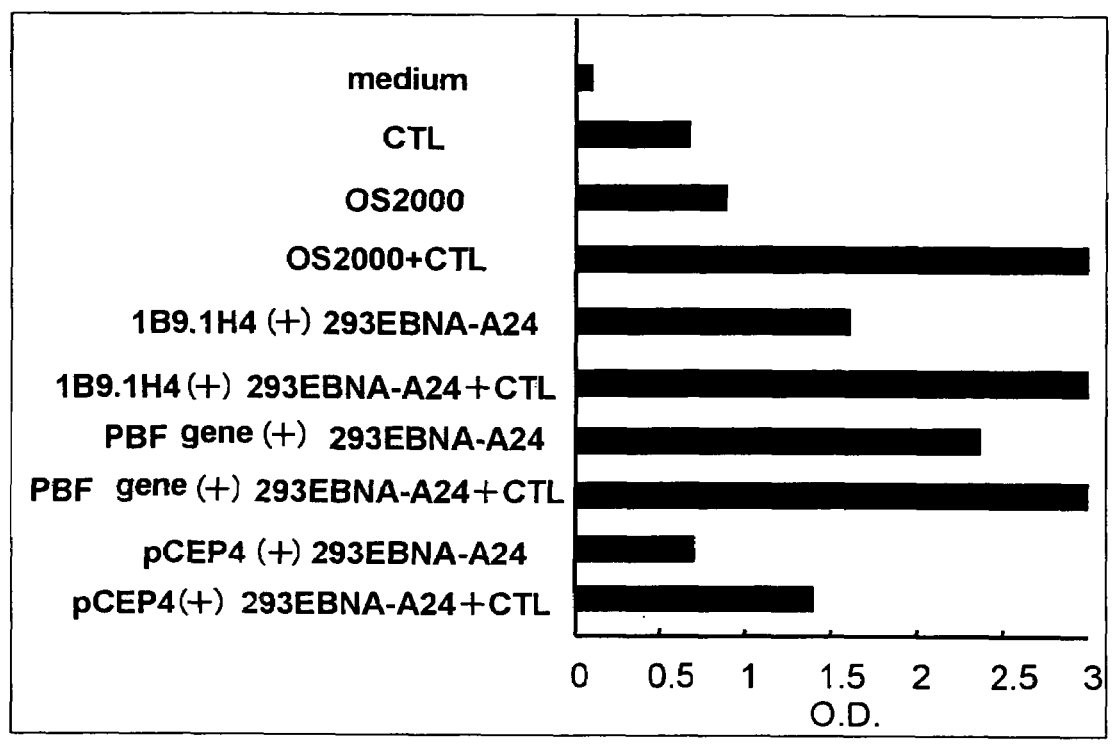

FIG. 3 is a graph showing the reactivity of CTL (TcOS2000cl-303) to 293-EBNA-A24 measured by LDH release assay, wherein the cell was transfected with 1B9.1H4 or PBF gene and allowed to express the same. In the figure, the abscissa axis represents the absorbance at 490 nm.

Figure 4:
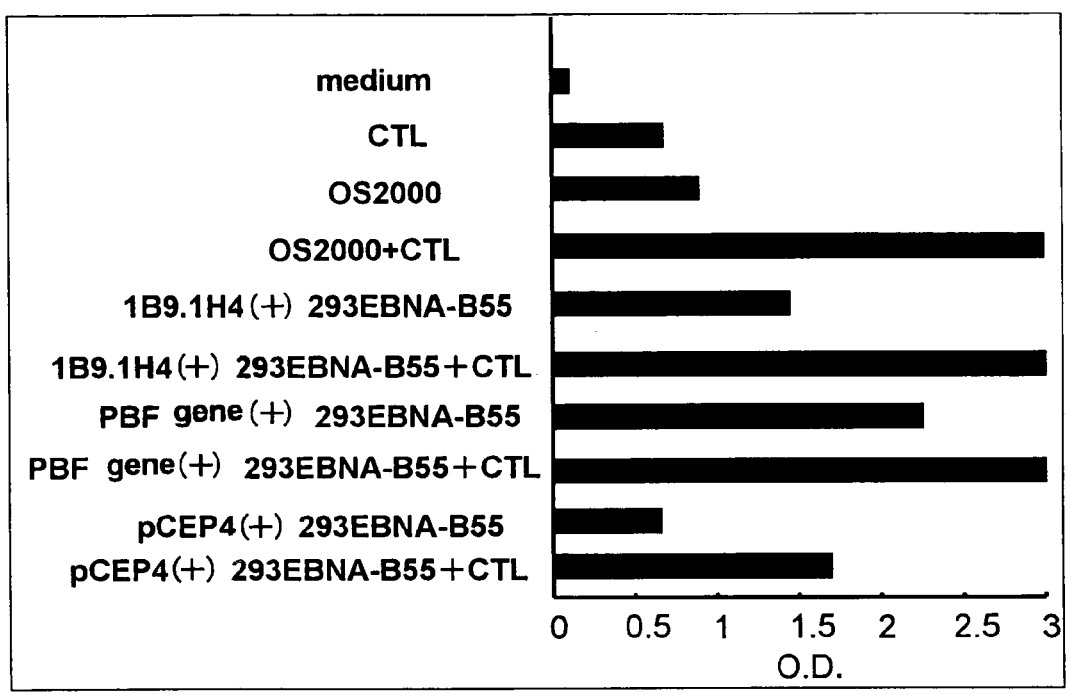

FIG. 4 is a graph showing the reactivity of CTL (TcOS2000cl-303) to 293-EBNA-B55 measured by LDH release assay, wherein the cell was transfected with 1B9.1H4 or PBF gene and allowed to express the same. In the figure, the abscissa axis represents the absorbance at 490 nm.

Figure 5:
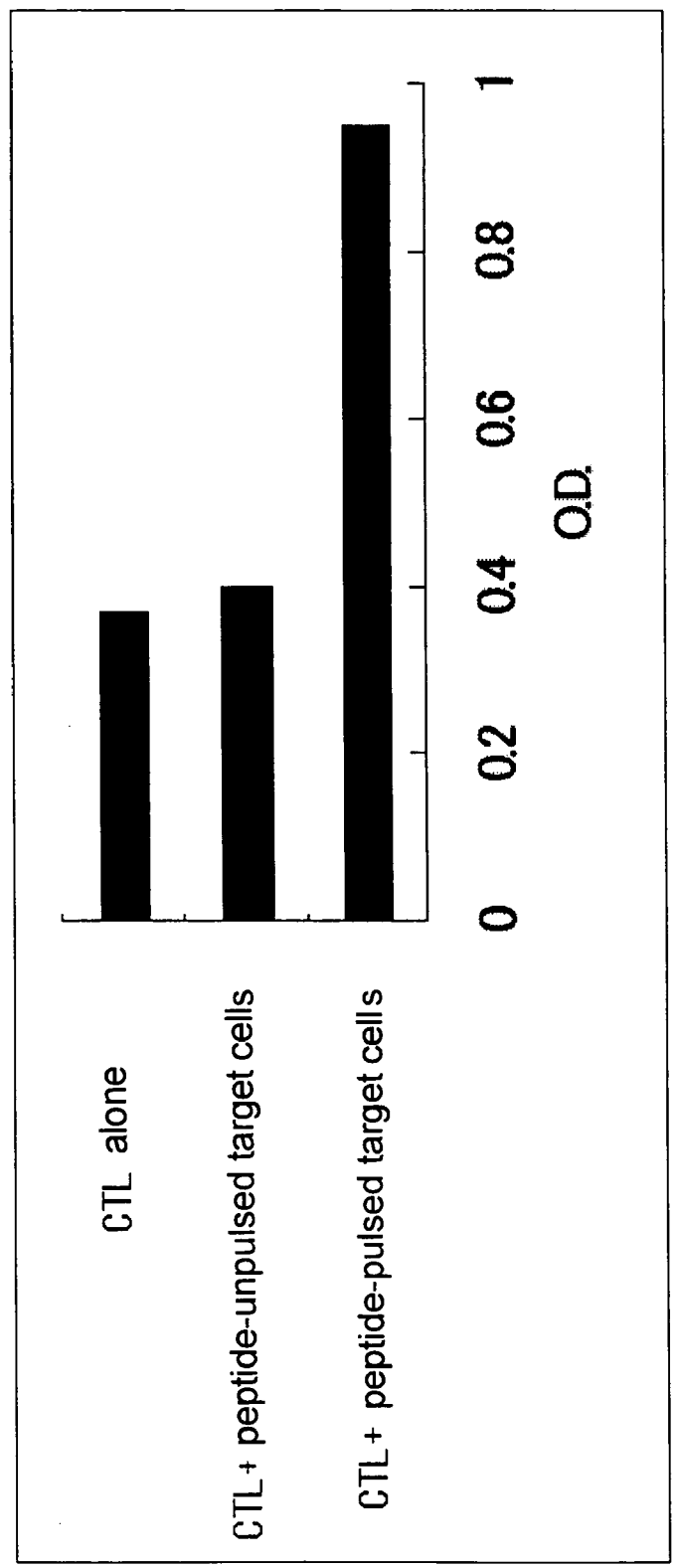

FIG. 5 is a graph showing the reactivity of CTL (TcOS2000cl-303) to 293-EBNA-B55 measured by LDH release assay, wherein the cell was pulsed with the peptide shown in SEQ ID NO: 46. In the figure, the abscissa axis represents the absorbance at 490 nm.

Figure 6:
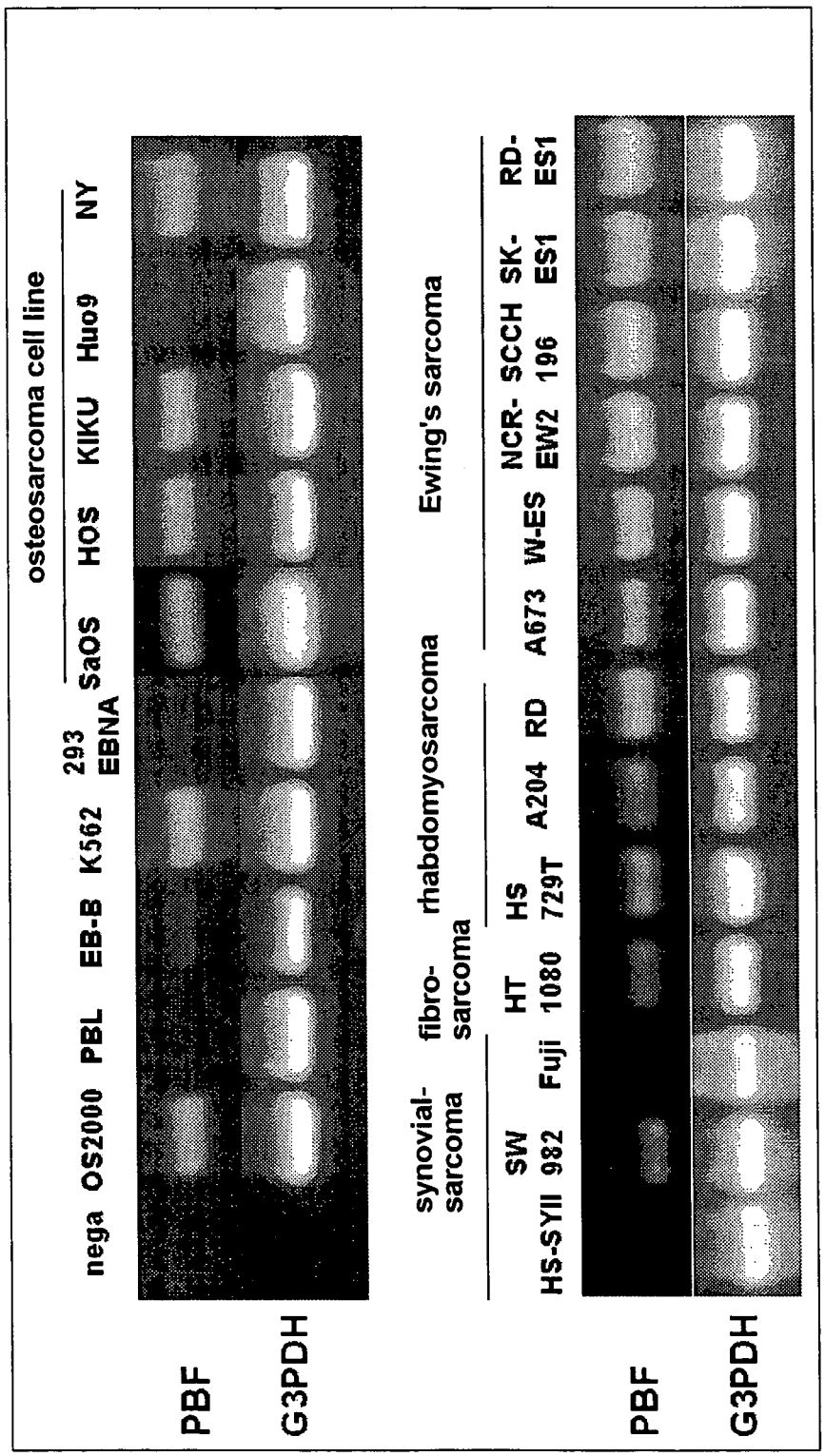

FIG. 6 is a photograph showing the expression of a gene encoding tumor antigen protein PBF in various types of cells analyzed by the reverse transcription-PCR (RT-PCR). In the figure, OS2000 is an osteosarcoma cell line, PBL is normal peripheral blood lymphocyte cell, EB-B is EBV transform B cell, K562 is chronic myelocytic leukemia cell line, and 293EBNA is human renal cell line transformed with adenovirus. SaOS, HOS, KIKU, Huo9 and NY represent osteosarcoma cell lines. HS-SYII, SW982 and Fuji represent synovial sarcoma cell line. HT1080 represents fibrosarcoma cell line. HS729T, A204 and RD represent rhabdomyosarcoma cell lines. Further, A673, W-ES, NCR-EW2, SCCH196, SK-ES1 and RD-ES1 represent Ewing's sarcoma cell lines. The upper panel represents the expression of PBF gene, and the lower panel the expression of G3PDH gene that is used as a positive control.

BEST MODE FOR CARRYING OUT THE INVENTION

1) Protein of the Present Invention

The protein contained in the inducer of CTL of the present invention, which protein may be referred to as "protein of the present invention", comprises the same or substantially the same amino acid sequence as that shown in SEQ ID NO: 2. The protein of the present invention may be a protein originated from natural source (e.g., osteosarcoma cell line) or a recombinant protein.

The amino acid sequence shown in SEQ ID NO: 2 is registered with the GenBank database under Accession No. AF263928, and represents human papillomavirus binding factor (PBF) disclosed in Virology 293, 103-117 (2002).

The aforementioned "a protein comprising the same amino acid sequence as that shown in SEQ ID NO:2 (i.e., a protein comprising the amino acid sequence shown in SEQ ID NO:2)" specifically include a protein consisting of the amino acid sequence shown in SEQ ID NO:2 and a protein consisting of an amino acid sequence wherein the amino acid sequence of SEQ ID NO:2 has an additional amino acid sequence attached to the N and/or C terminus.

The aforementioned "a protein comprising substantially the same amino acid sequence as that shown in SEQ ID NO:2" specifically include the following proteins (a) to (c).

(a) a protein comprising an amino acid sequence wherein one or more amino acids are deleted, substituted and/or added in the amino acid sequence shown in SEQ ID NO: 2, and being characterized by that a cell expressing the protein is recognized by CTLs;

(b) a protein comprising an amino acid sequence having at least 70% sequence identity with the amino acid sequence shown in SEQ ID NO: 2, and being characterized by that a cell expressing the protein is recognized by CTLs; and (c) a protein being encoded by a polynucleotide capable of hybridizing to a complementary strand of polynucleotide encoding the amino acid sequence shown in SEQ ID NO: 2 under stringent conditions, and being characterized by that a cell expressing the protein is recognized by CTLs.

Preferred examples include a protein consisting of a substantially the same amino acid sequence as that shown in SEQ ID NO: 2. Examples of such a protein consisting of a substantially the same amino acid sequence as that shown in SEQ ID NO: 2 include the proteins (a') to (c') below.

(a') a protein consisting of an amino acid sequence wherein one or more amino acids are deleted, substituted and/or added in the amino acid sequence shown in SEQ ID NO: 2, and being characterized by that a cell expressing the protein is recognized by CTLs;

(b') a protein consisting of an amino acid sequence having at least 70% sequence identity with the amino acid sequence shown in SEQ ID NO: 2, and being characterized by that a cell expressing the protein is recognized by CTLs; and (c') a protein being encoded by a polynucleotide capable of hybridizing to a complementary strand of polynucleotide encoding the amino acid sequence shown in SEQ ID NO: 2 under stringent conditions, and being characterized by that a cell expressing the protein is recognized by CTLs.

The phrase "protein comprising an amino acid sequence wherein one or more amino acids are deleted, substituted and/or added in the amino acid sequence shown in SEQ ID NO: 2" refers to so-called modified (variant) proteins produced artificially or allele variants present in a living body.

In this respect, there is no limitations regarding the number or position of modification (mutation) in the protein as far as the activity of the protein of the present invention is maintained. Criteria based on which one can determine the number or position of amino acid residue to be deleted, substituted and/or added without reducing the activity can be obtained using a computer program well known in the art, such as DNA Star software. For example, the number of mutation would typically be within 10%, preferably 5% of the total amino acid residues. Furthermore, the amino acid used for substitution preferably has similar characteristics to the one to be substituted in view of retention of structure, which characteristics include polarity, charge, solubility, hydrophobicity, hydrophilicity, amphipathicity, etc. For instance, Ala, Val, Leu, Ile, Pro, Met, Phe and Trp are classified into nonpolar amino acids; Gly, Ser, Thr, Cys, Tyr, Asn and Gln into non-charged amino acids; Asp and Glu into acidic amino acids; and Lys, Arg and His into basic amino acids. One of ordinary skill in the art can select an appropriate amino acid(s) falling within the same group on the basis of these criteria.

Examples of "a protein comprising an amino acid sequence having at least 70% sequence identity with the amino acid sequence shown in SEQ ID NO: 2" in (b) above include proteins comprising amino acid sequences having at least about 70%, preferably, about 80%, more preferably, about 90%, and further more preferably about 95% sequence identity with the amino acid sequence shown in SEQ ID NO: 2, and specifically, proteins consisting of a partial amino acid sequence of SEQ ID NO:2.

The term "sequence identity" herein used refers to the identity and homology between two proteins. The "sequence identity" is determined by comparing two sequences aligned optimally over the regions corresponding to the sequences to be compared. In this context, the both proteins to be compared may have addition or deletion (e.g., "gap") in their sequences for optimum alignment. Such sequence identity can be calculated by preparing alignment using, for example, Vector NTI, ClustalW algorithm (Nucleic Acid Res., 22 (22): 4673-4680(1994)). The sequence identity can be determined using software for sequence analysis, specifically, Vector NTI or GENETYX-MAC, or a sequencing tool provided by a public database.

Examples of "a polynucleotide capable of hybridizing to a complementary strand of polynucleotide encoding the amino acid sequence shown in SEQ ID NO: 2 under stringent conditions" in (c) include polynucleotides comprising base sequences having at least about 40%, preferably, about 60%, more preferably, about 70%, still more preferably about 80%, further more preferably about 90%, and most preferably, about 95% sequence identity with a polynucleotide encoding the amino acid sequence shown in SEQ ID NO: 2. Specifically, examples include polynucleotides comprising base sequences having at least about 40%, preferably, about 60%, more preferably, about 70%, still more preferably about 80%, further more preferably about 90%, and most preferably, about 95% sequence identity with the base sequence of SEQ ID NO: 1, the base sequence at positions 337-1878 of SEQ ID NO: 1, or the base sequence of SEQ ID NO:3. More specifically, examples include nucleic acids consisting of partial sequences of the base sequences of SEQ ID NO: 1, positions 337-1878 of SEQ ID NO: 1 or SEQ ID NO:3.

Hybridization can be conducted according to a method known per se or a method equivalent thereto, for example, that described in a fundamental text such as "*Molecular Cloning* 2nd Edt. Cold Spring Harbor Laboratory Press (1989)", and the like. Also, it can be performed using a commercially available library according to the instructions attached thereto.

The "stringent conditions" herein used can be determined on the basis of the melting temperature (Tm) of nucleic acids forming a complex with or binding to probe as described in literatures (Berger and Kimmel, 1987, "*Guide to Molecular Cloning Techniques Methods in Enzymology*", Vol. 152, Academic Press, San Diego Calif.; or "*Molecular Cloning*" 2nd Edt. Cold Spring Harbor Laboratory Press (1989), ibid.).

For example, hybridization can be carried out in a solution containing 6×SSC (20×SSC means 333 mM sodium citrate, 333 mM NaCl), 0.5% SDS and 50% formamide at 42° C., or in a solution containing 6×SSC (without 50% formamide) at 65° C.

Washing after hybridization can be conducted under a condition around "1×SSC, 0.1% SDS, 37° C.". The complementary strand preferably remains bound to the target sense when washed under such washing conditions. More stringent hybridization conditions may involve washing under the conditions of around "0.5×SSC, 0.1% SDS, 42° C." and still more stringent hybridization conditions involve washing conditions of around "0.1×SSC, 0.1% SDS, 65° C.", although it is not limited thereto.

The protein of the present invention has an activity of substantially the same quality as that having amino acid sequence of SEQ ID NO:2. The term "activity of substantially the same quality" refers to the characteristic future that cells expressing the protein are recognized by CTLs, that is, the said cells exhibit reactivity to CTLs, in other words, the protein of the present invention or tumor antigen peptide derived therefrom activates or induces CTLs.

In this respect, the term "cells" are preferably those expressing HLA antigen. Accordingly, the said phrase "activity of substantially the same quality" more specifically refers to the characteristics that, when the protein of the present invention is expressed in cells expressing HLA antigens such as HLA-A24 or HLA-B55, a complex between a tumor antigen peptide originated from the protein of the present invention and an HLA antigen is presented on the cell surface and consequently the cells are recognized by CTLs, in other words, CTLs are activated (induced).

Such characteristics of the protein of the present invention can be easily determined by a method known or a method equivalent thereto, such as $^{51}$Cr release assay (*J. Immunol.*, 159: 4753, 1997), LDH release assay using LDH Cytotoxicity Detection Kit (Takara Bio, Inc.), measurement of cytokines, and the like. The detailed protocol of assay will hereinafter be illustrated.

First, a host cell such as 293-EBNA cell (Invitrogen) is co-transfected with an expression vector comprising a DNA encoding the protein of the present invention and an expression vector comprising a DNA encoding HLA antigen. The DNA encoding HLA antigen includes a DNA encoding HLA-A24 antigen or HLA-B55 antigen. Examples of DNA encoding HLA-A24 antigen include HLA-A2402 cDNA (*Cancer Res.*, 55: 4248-4252 (1995), Genbank Accession No. M64740. Examples of DNA encoding HLA-B55 antigen include HLA-B5502cDNA (GenBank Acc. No. M77777, *J. Immunol.*, 148 (4), 1155-1162 (1992)).

The transfection above can be conducted by Lipofectin method using lipofectamine reagent (GIBCO BRL), and the like. Then, CTLs restricted to the HLA antigen used are added and allowed to react, followed by measurement of various cytokines (for example, IFN-γ) produced by CTLs reacted or activated by, for example, ELISA. CTLs usable herein include those prepared by stimulating peripheral blood lymphocytes with the protein of the present invention (SEQ ID NO: 2) or those established according to the method of Int. *J. Cancer,* 39, 390-396, 1987, *N. Eng. J. Med,* 333, 1038-1044, 1995, or the like.

The CTL induction activity of the protein of the present invention can also be examined in vivo by an assay where human model animals are used (WO 02/47474; *Int. J. Cancer.* 100, 565-570 (2002)).

The protein of the present invention can be prepared by a method known per se that used for purifying protein from natural products (e.g., osteosarcoma cell line, renal cancer cell line) or by a method hereinafter described comprising culturing transformants carrying a nucleic acid comprising a polynucleotide encoding the protein of the present invention.

2) Peptide of the Present Invention

The peptide contained in the inducer of CTL of the present invention, which peptide may be referred to as "peptide of the present invention", is a partial peptide of the protein of the present invention as defined above and, when bound to HLA antigen, is recognized by CTLs. Thus, the peptide of the present invention may be any one existing at any positions of the amino acid sequence of the protein of the present invention and of any length, as long as said peptide consists of a partial amino acid sequence of the protein of the present invention as defined above and can form a complex with an HLA antigen that is recognized by CTLs.

The peptide of the present invention can be identified by synthesizing a candidate peptide, which is a partial fragment of the protein of the present invention, and subjected to an assay to examine whether or not CTLs recognize a complex between said candidate peptide and HLA antigen, that is, whether or not the candidate peptide has the activity as a tumor antigen peptide.

Synthesis of a peptide can be conducted according to processes generally used in the field of peptide chemistry. Such a method can be found in literatures including *Peptide Synthesis*, Interscience, New York, 1966; *The Proteins*, Vol. 2, Academic Press Inc., New York, 1976; *Peptide Synthesis*, Maruzen, Inc., 1975; *Peptide-Gosei no Kiso to Jikken*, Maruzen, Inc., 1985; and *Iyakuhin no Kaihatsu* (Zoku), Vol. 14, Peptide Synthesis, Hirokawa-syoten, 1991.

The method for identification of the tumor antigen peptide of the present invention will hereinafter be described in detail.

The regularity (motif) in the amino acid sequence of a tumor antigen peptide that binds to HLA molecule and is presented has been elucidated in relation to HLA-A1, -A0201, -A0204, -A0205, -A0206, -A0207, -A11, -A24, -A31, -A6801, -B7, -B8, -B2705, -B37, -Cw0401, -Cw0602. See, *Immunogenetics*, 41: p. 178, 1995, etc. For example, motifs for HLA-A24 are known to have an amino acid sequence of 8-11 amino acids, wherein the position 2 amino acid is tyrosine, phenylalanine, methionine or tryptophan, and the C-terminal amino acid phenylalanine, leucine, isoleucine, tryptophan or methionine (*J. Immunol.*, 152, p3913, 1994, *Immunogenetics*, 41: p178, 1995. *J. Immunol.*, 155 : p4307, 1994). As for motifs for HLA-A2, those listed in Table 1 are known (*Immunogenetics*, 41, p178, 1995, *J. Immunol.*, 155: p4749, 1995).

TABLE 1

| HLA-A2 type | 2nd amino acid from N-terminus | amino acid at C-terminus |
|---|---|---|
| HLA-A0201 | L, M | V, L |
| HLA-A0204 | L | L |
| HLA-A0205 | V, L, I, M | L |
| HLA-A0206 | V, Q | V, L |
| HLA-A0207 | L | L |

* All the peptides are 8-11 in amino acid length.

Recently, it has become possible to search peptide sequences expected to be capable of binding to HLA antigens via the internet using BIMAS software.

As for the length of the peptides, analysis of antigen peptides binding to various HLA molecules revealed that it is generally about 8 to 14 amino acids (*Immunogenetics*, 41: 178, 1995). However, in the cases of HLA-DR, DP, -DQ, peptides consist of 14 amino acids or more are known.

It is easy to select the peptide portions related to the motifs in the protein of the present invention. For example, search for the sequences expected to be capable of binding to HLA antigen may be facilitated by means of BIMAS software. The peptide of the present invention can be identified by synthesizing the selected candidate peptide by the above-mentioned method, and examining whether or not said candidate peptide binds to HLA antigen and is recognized by CTLs, that is, whether or not the candidate peptide has an activity as a tumor antigen peptide.

Specifically, identification can be done by the method descried in *J. Immunol.*, 154, p2257, 1995. Thus, a candidate peptide is added to stimulate in vitro peripheral blood lymphocytes isolated from a human positive for an HLA antigen that is expected to present the candidate peptide. When CTLs specifically recognizing the HLA-positive cells pulsed with the candidate peptide are induced, said candidate peptide is possibly a tumor antigen peptide. The presence or absence of induction of CTLs may be examined by, for example, measuring the amount of various cytokines (e.g., IFN-γ) produced by CTLs in response to the antigen-presenting cells using ELISA or the like. Alternatively, the induction of CTLs can also be examined by $^{51}$Cr release assay wherein cytotoxicity of CTLs on antigen-presenting cells labeled with $^{51}$Cr is measured (*Int. J. Cancer*, 58: p317, 1994).

Furthermore, the induction of CTLs can be examined by pulsing a cell such as 293-EBNA cell (Invitrogen) with a candidate peptide, to which cell an expression plasmid expressing a cDNA encoding HLA antigen of a type expected to present the candidate peptide has been introduced, reacting the cell with CTLs restricted to HLA antigen of the aforementioned type that is expected to present the said candidate peptide, and measuring various cytokines (e.g., IFN-γ) produced by the CTLs (*J. Exp. Med.*, 187: 277, 1998).

Examples of HLA antigen include a HLA-A24 antigen and HLA-B55 antigen. To select HLA-A24-restricted tumor antigen peptide, HLA-A2402 cDNA (*Cancer Res.*, 55: 4248-4252 (1995), Genbank Accession No. M64740) can be used as the cDNA encoding HLA antigen. To select HLA-B55-restricted tumor antigen peptide, HLA-B5502 cDNA (GenBank Acc. No. M77777, *J. Immunol.*, 148 (4), 1155-1162 (1992)) can be used as the cDNA encoding HLA antigen.

As for CTLs, in addition to those obtained by stimulating human peripheral blood lymphocytes with a peptide, those established by a method described in literatures (*Int. J. Cancer*, 39, 390-396, 1987; *N. Eng. J. Med*, 333, 1038-1044, 1995) may be used.

The in vivo activity of the peptide of the present invention can be determined by an assay which uses an animal model for human (WO 02/47474, *Int J. Cancer* 100, 565-570 (2002)).

In the above case, the regularity (motif) of the sequence of tumor antigen peptide is known; however, when the motif of a peptide is unknown, as in the case of HLA-B55, the tumor antigen peptide of the present invention can be identified according to the method described in, for example, WO97/46676 or Example 3 below, only if CTL cell lines capable of recognizing a complex between said HLA-B55 and tumor antigen peptide is available.

Specific examples of a peptide of the present invention include partial peptides derived from the protein of the present invention consisting of the amino acid sequence shown in SEQ ID NO: 2, and capable of binding to HLA antigen and being recognized by CTLs. Preferred examples include peptides capable of binding to HLA-A24 or HLA-B55 antigen, considering the HLA antigen to which the peptide of the present invention binds.

More specifically, examples of HLA-A24-binding tumor antigen peptide include a peptide (i.e., a peptide consisting of any one of amino acid sequences shown in SEQ ID NO: 6-45) having any one of amino acid sequences listed in Table 2 (9 amino acids) and Table 3 (10 amino acids), and being recognized by CTLs when bound to HLA-A24 antigen.

TABLE 2

| Position | Amino acid sequence | SEQ ID No. |
|---|---|---|
| 145-153 | Ala Tyr Arg Pro Val Ser Arg Asn Ile | SEQ ID NO: 6 |
| 320-328 | Asp Phe Tyr Tyr Thr Glu Val Gln Leu | SEQ ID NO: 7 |
| 254-262 | Gly Phe Glu Thr Asp Pro Asp Pro Phe | SEQ ID NO: 8 |
| 240-248 | Lys Tyr Leu Gly Asp Ala Phe Gly Ser | SEQ ID NO: 9 |
| 12-20 | Arg Ser Leu Leu Gly Ala Arg Val Leu | SEQ ID NO: 10 |

TABLE 2-continued

| Position | Amino acid sequence | SEQ ID No. |
|---|---|---|
| 30-38 | Ala Ala Pro Pro Ser Glu Pro Leu Leu | SEQ ID NO: 11 |
| 424-432 | Ile Tyr Thr Ser Val Ser Trp Ala Ala | SEQ ID NO: 12 |
| 105-113 | Thr Val Trp Leu Leu Glu Gln Lys Leu | SEQ ID NO: 13 |
| 234-242 | His Pro Gln Ala Ser Pro Lys Tyr Leu | SEQ ID NO: 14 |
| 440-448 | Leu Ser Pro Val Arg Ser Arg Ser Leu | SEQ ID NO: 15 |
| 279-287 | Met Tyr Lys Cys Leu Trp Pro Asn Cys | SEQ ID NO: 16 |
| 283-291 | Leu Trp Pro Asn Cys Gly Lys Val Leu | SEQ ID NO: 17 |
| 54-62 | Cys Gln Glu Gln Pro Lys Glu Val Leu | SEQ ID NO: 18 |
| 432-440 | Ala Ala Pro Ser Ala Ala Cys Ser Leu | SEQ ID NO: 19 |
| 101-109 | Glu Gly Gln Val Thr Val Trp Leu Leu | SEQ ID NO: 20 |
| 169-177 | Met Ala Ala Met Val Leu Thr Ser Leu | SEQ ID NO: 21 |
| 129-137 | Gly Pro Cys Pro Gln Ala Pro Pro Leu | SEQ ID NO: 22 |
| 354-362 | Ala Pro Thr Pro Ser Met Thr Gly Leu | SEQ ID NO: 23 |
| 503-511 | Arg Trp Lys Lys Ala Cys Gln Arg Phe | SEQ ID NO: 24 |
| 29-37 | Ser Ala Ala Pro Pro Ser Glu Pro Leu | SEQ ID NO: 25 |

TABLE 3

| Position | Amino acid sequence | SEQ ID No. |
|---|---|---|
| 84-93 | Trp Tyr Gly Gly Gln Glu Cys Thr Gly Leu | SEQ ID NO: 26 |
| 409-418 | Ala Tyr Gln Ala Leu Pro Ser Phe Gln Ile | SEQ ID NO: 27 |
| 254-263 | Gly Phe Glu Thr Asp Pro Asp Pro Phe Leu | SEQ ID NO: 28 |
| 118-127 | Arg Val Glu Glu Val Trp Leu Ala Glu Leu | SEQ ID NO: 29 |
| 415-424 | Ser Phe Gln Ile Pro Val Ser Pro His Ile | SEQ ID NO: 30 |
| 81-90 | Val Tyr Val Trp Tyr Gly Gly Gln Glu Cys | SEQ ID NO: 31 |
| 104-113 | Val Thr Val Trp Leu Leu Glu Gln Lys Leu | SEQ ID NO: 32 |
| 99-108 | Trp Met Glu Gly Gln Val Thr Val Trp Leu | SEQ ID NO: 33 |

TABLE 3-continued

| Position | Amino acid sequence | SEQ ID No. |
|---|---|---|
| 503-512 | Arg Trp Lys Lys Ala Cys Gln Arg Phe Leu | SEQ ID NO: 34 |
| 362-371 | Leu Pro Leu Ser Ala Leu Pro Pro Pro Leu | SEQ ID NO: 35 |
| 295-304 | Val Gly Ile Lys Arg His Val Lys Ala Leu | SEQ ID NO: 36 |
| 274-283 | Asn Ser Val Lys Val Met Tyr Lys Cys Leu | SEQ ID NO: 37 |
| 128-137 | Gln Gly Pro Cys Pro Gln Ala Pro Pro Leu | SEQ ID NO: 38 |
| 404-413 | Ile Gln Ala Asp His Ala Tyr Gln Ala Leu | SEQ ID NO: 39 |
| 168-177 | Met Met Ala Ala Met Val Leu Thr Ser Leu | SEQ ID NO: 40 |
| 424-433 | Ile Tyr Thr Ser Val Ser Trp Ala Ala Ala | SEQ ID NO: 41 |
| 489-498 | Val Tyr Gly Ile Glu His Arg Asp Gln Trp | SEQ ID NO: 42 |
| 439-448 | Ser Leu Ser Pro Val Arg Ser Arg Ser Leu | SEQ ID NO: 43 |
| 431-440 | Ala Ala Ala Pro Ser Ala Ala Cys Ser Leu | SEQ ID NO: 44 |
| 455-464 | Gln Pro Ala Pro Ala Met Lys Ser His Leu | SEQ ID NO: 45 |

Further, HLA-B55-restricted tumor antigen peptide includes a peptide having the amino acid sequence: Cys Thr Ala Cys Arg Trp Lys Ala Cys Gln Arg (SEQ ID NO: 46). In addition, a peptide consisting of 9-, 10- or 11-amino acid portion of the peptide above, that is, a peptide having any one of amino acid sequences listed below, which peptide can be recognized by CTLs when bound to HLA-B55 antigen, is also included.

Cys Thr Ala Cys Arg Trp Lys Lys Ala (SEQ ID NO: 47)

Thr Ala Cys Arg Trp Lys Lys Ala Cys (SEQ ID NO: 48)

Ala Cys Arg Trp Lys Lys Ala Cys Gln (SEQ ID NO: 49)

Cys Arg Trp Lys Lys Ala Cys Gln Arg (SEQ ID NO: 50)

Cys Thr Ala Cys Arg Trp Lys Lys Ala Cys (SEQ ID NO: 51)

Thr Ala Cys Arg Trp Lys Lys Ala Cys Gln (SEQ ID NO: 52)

Ala Cys Arg Trp Lys Lys Ala Cys Gln Arg (SEQ ID NO: 53)

Cys Thr Ala Cys Arg Trp Lys Lys Ala Cys Gln (SEQ ID NO: 54)

Thr Ala Cys Arg Trp Lys Lys Ala Cys Gln Arg (SEQ ID NO: 55)

The peptide of the present invention includes one consisting of not only a part of the amino acid sequence of SEQ ID NO: 2 but also a part of proteins of the present invention having an amino acid sequence substantially the same as SEQ ID NO: 2, subject that said peptide has a characteristic of binding to HLA antigen and being recognized by CTLs. Thus, a modified peptide (hereinafter, the modified peptide may be referred to as "variant peptide") consisting of a part of the protein of the present invention having an amino acid sequence wherein the amino acid sequence shown in SEQ ID NO: 2 is partly modified (by deletion, substitution and/or addition of amino acid(s)) also falls within the scope of the present invention, subject that said peptide has a characteristic of binding to HLA antigen and being recognized by CTLs. Specifically, a variant peptide having an amino acid sequence wherein at least one amino acid modification has been introduced into the amino acid sequence of the peptide of the present invention which consists of a partial amino acid sequence of the protein of the present invention, specifically the amino acid sequence of SEQ ID NO: 2, and being capable of binding to HLA antigen and recognized by CTLs falls within the scope of the present invention.

The "modification" of amino acid residues means substitution, deletion and/or addition of amino acid including addition to the N- and/or C-terminus of peptide, preferably substitution of amino acid. When the modification involves amino acid substitution, the number or position of amino acid to be substituted can be selected arbitrarily; however, it is preferred that the substitution involves 1 to several amino acids since the tumor antigen peptides are generally about 8-14 amino acids in length.

Variant peptides of the present invention are preferably 8 to 14 amino acids in length. However, in the cases of HLA-DR, -DP, -DQ, peptides consist of 14 amino acids or more are known.

As mentioned above, motifs for antigen peptides that bind to an HLA and presented are known in regard to certain HLA types, such as HLA-A1, -A0201, -A0204, -A0205, -A0206, -A0207, -A11, -A24, -A31, -A6801, -B7, -B8, -B2705, -B37, -Cw0401 and -Cw0602. Further, it is possible to search for peptide sequences that are expected to be able to bind to HLA antigen via internet. Thus, one can prepare the variant peptides above on the basis of these motifs and the like.

For example, as hereinbefore described, motifs of antigen peptides capable of binding to HLA-A24 and being presented are known that, in the 8-11 amino acid peptide, the amino acid at position 2 is tyrosine, phenylalanine, methionine or tryptophan, and the C terminal amino acid is phenylalanine, leucine, isoleucine, tryptophan or methionine (J. Immunol., 152: p 3913, 1994; Immunogenetics, 41: p 178, 1995; J. Immunol., 155: p 4307, 1994). As for HLA-A2, the motifs listed in Table 1 above are known. Furthermore, there are published via internet certain peptide. sequences that are expected to be able to bind to HLA antigen Accordingly, amino acids having a similar characteristic to those available for the motif above are acceptable. Thus, the present invention includes variant peptides comprising an amino acid sequence wherein an amino acid(s) at position(s) available for substitution in light of motif (in the case of HLA-A24 and HLA-A2, position 2 and C-terminus) is substituted by other amino acid, preferably, an amino acid expected to have binding activity as a result of internet search, and having an activity of binding to HLA and being recognized by CTLs.

More preferably, the present invention includes variant peptides comprising an amino acid sequence wherein an amino acid(s) at that position(s) is substituted by any amino acid(s) known to be available in light of motif and having the said activity. Thus, in the case of HLA-A 24-restricted peptides, as shown in SEQ ID NO: 6-45, examples of variant peptides include those having an amino acid sequence wherein the amino acid at position 2 is substituted by tyrosine, phenylalanine, methionine or tryptophan, and/or the C terminal amino acid by phenylalanine, leucine, isoleucine, tryptophan or methionine, and having the aforementioned activity are included. Above all, a peptide wherein the amino acid at the second position is substituted by tyrosine is more preferred.

The peptide of the present invention includes an epitope peptide comprising the above-mentioned peptide of the present invention.

Recently, a peptide ("epitope peptide") composed of multiple (plural) CTL epitopes (antigen peptides) linked together has been shown to induce CTLs efficiently For example, it has been reported that a peptide (about 30-mer) wherein CTL epitopes each restricted to HLA-A2-, -A3, -A11, B53 originated from tumor antigen protein PSA are ligated together induced in vivo CTLs specific for respective CTL epitopes (*Journal of Immunology* 1998, 161: 3186-3194).

In addition, a peptide (epitope peptide) wherein a CTL epitope and a helper epitope are ligated has been shown to induce CTLs efficiently. In this context, "helper epitope" means a peptide capable of activating a CD4-positive T cells (*Immunity.*, 1:751, 1994), and examples thereof include HBVc128-140 of hepatitis B virus origin, TT947-967 of tetanus toxin origin, etc. CD4+ T cells activated by said helper epitope exert activities including induction and maintenance of CTLs, and activation of effectors such as macrophages, etc, and hence are considered to be important in the immunological anti-tumor response. As a concrete example of a peptide composed of a helper epitope and a CTL epitope linked together, it is reported that a DNA (minigene) composed of HBV-originated HLA-A2-restricted tumor antigen peptides (6 peptides), HLA-A11-restricted tumor antigen peptides (3 peptides) and a helper epitope induced in vivo CTLs directed to the respective epitopes efficiently (*Journal of Immunology* 1999, 162: 3915-3925). Practically, a peptide wherein a CTL epitope (tumor antigen peptide corresponding to position 280-288 of melanoma antigen gp100) and a helper epitope (tetanus toxin-originated T helper epitope) are ligated has been subjected to clinical test (*Clinical Cancer Res.*, 2001, 7:3012-3024).

Accordingly, the peptide of the present invention also includes a peptide (epitope peptide) consisting of multiple epitopes including the peptide of the present invention ligated therein and having an activity of inducing CTLs.

In this respect, the "epitope peptide" is defined as a peptide that is (a) a peptide consisting of two or more CTL epitopes (tumor antigen peptides) ligated therein, or (b) a peptide consisting of a CTL epitope and a helper epitope ligated therein, which is processed in an antigen-presenting cell to give a tumor antigen peptide, which tumor antigen peptide is then presented by said cell and induces CTLs.

When the epitope to be ligated to the peptide of the present invention is a CTL epitope, examples of CTL epitopes usable include those derived from the amino acid sequence shown in SEQ ID NO: 2 which are restricted to HLA-A1, -A0201, -A0204, -A0205, -A0206, -A0207, -A11, -A24, -A31, -A6801, -B7, -B8, -B2705, -B37,-B55, -Cw0401, -Cw0602, and the like. CTL epitopes originated from other tumor antigen proteins are also usable. Plural number of CTL epitopes can be linked together, and the length of a CTL epitope may be about 8-14 amino acids based on the analysis of antigen peptides binding to various HLA molecules (*Immunogenetics*, 41: 178, 1995).

When the epitope to be ligated to the peptide of the present invention is a helper epitope, examples of helper epitopes usable include the aforementioned HBVc128-140 of hepatitis B virus origin, TT947-967 of tetanus toxin origin, etc. The helper epitope may be about 13-30 amino acids, preferably, about 13-17 amino acids in length.

The peptide (epitope peptide) composed of multiple epitopes ligated therein can be prepared by aforementioned usual method for peptide synthesis. It can also be prepared by a usual method for DNA synthesis and genetic engineering on the basis of sequence information of a polynucleotide encoding epitope peptide composed of multiple epitopes ligated therein. That is, an intended epitope peptide wherein multiple epitopes are ligated can be prepared by inserting a polynucleotide encoding the polynucleotide into a known expression vector, transforming a host cell with the resultant recombinant expression vector, culturing the transformants, and recovering the peptide from the culture. These processes can be conducted according to, for example, a method described in a literature (*Molecular Cloning*, T. Maniatis et al., CSH Laboratory (1983), DNA Cloning, DM. Glover, IRL PRESS (1985)).

The so produced epitope peptide wherein multiple epitopes are ligated can be examined for the CTL-inducing activity in vitro by means of an assay as mentioned above, or in vivo by means of an assay described in WO02/47474 or *Int J. Cancer.* 100, 565-570 (2002) using a model animal for human.

Also, the amino group of the N-terminal amino acid or the carboxyl group of the C-terminal amino acid of the peptides of the present invention can be modified. The peptides undergone such modification also fall within the scope of the present invention.

Examples of a group for the modification of amino group of the N-terminal amino acid include 1 to 3 groups selected from $C_{1-6}$ alkyl group, phenyl group, cycloalkyl group and acyl group. Acyl groups specifically includes $C_{1-6}$ alkanoyl group, $C_{1-6}$ alkanoyl group substituted by phenyl group, carbonyl group substituted by $C_{5-7}$ cycloalkyl group, $C_{1-6}$ alkylsulfonyl group, phenylsulfonyl group, $C_{2-6}$ alkoxycarbonyl group, alkoxycarbonyl group substituted by phenyl group, carbonyl group substituted by $C_{5-7}$ cycloalkoxy group, phenoxycarbonyl group, etc.

Examples of peptides modified at the carboxyl group of C-terminal amino acid include esters and amides. Esters specifically include $C_{1-6}$ alkyl esters, $C_{0-6}$ alkyl esters substituted by phenyl group, $C_{5-7}$ cycloalkyl esters, etc. Amides specifically include amides, amides substituted by one or two $C_{1-6}$ alkyl groups, amides substituted by one or two $C_{0-6}$ alkyl groups that are substituted by phenyl group, amides forming 5- to 7-membered azacycloalkane inclusive of nitrogen atom of amide group, etc.

3) Polynucleotide of the Present Invention and Nucleic Acid Comprising the Polynucleotide The nucleic acid (hereinafter, it may be referred to as "nucleic acid of the present invention") contained in the inducer of CTL of the present invention comprises a polynucleotide (hereinafter, it may be referred to as "polynucleotide of the present invention") encoding the aforementioned protein of the present invention.

The polynucleotide of the present invention can be cDNA or mRNA, cRNA or genomic DNA of various cells or tissues originated from, for example, osteosarcoma or renal cancer, or synthetic DNA. It may be in either forms of single and double strands. Specifically, the polynucleotide of the present invention includes the followings:

(a) a polynucleotide comprising the base sequence shown in SEQ ID NO:1;

(b) a polynucleotide comprising the position 337-1878 of the base sequence shown in SEQ ID NO:1;

(c) a polynucleotide comprising a base sequence encoding the amino acid sequence shown in SEQ ID NO:2;

(d) a polynucleotide comprising the base sequence shown in SEQ ID NO:3; and a polynucleotide comprising substantially the same base sequence as polynucleotides (a)-(d).

In this respect, the base sequence shown in SEQ ID NO:1 is registered with GenBank database under Accession No. AF263928, and encodes human papillomavirus binding factor (PBF, SEQ ID NO:2) described in *Virology* 293, 103-117 (2002). The position 337-1878 is the open reading frame. The polynucleotide comprising the base sequence shown in SEQ ID NO: 3 is an analogous polynucleotide comprising the same base sequence portion(s) with the base sequence of SEQ ID NO: 1. Specifically, the partial sequence at position 1-1469 of the base sequence of SEQ ID NO:3 has 100% sequence identity with the partial sequence at position 704-1878 of the base sequence of SEQ ID NO:1, except for the 294 bp sequence that is present only in SEQ ID NO: 3.

Specifically, the above-defined polynucleotides (a)-(d), i.e., (a) a polynucleotide comprising the base sequence shown in SEQ ID NO: 1; (b) a polynucleotide comprising the position 337-1878 of the base sequence shown in SEQ ID NO: 1; (c) a polynucleotide comprising a base sequence encoding the amino acid sequence shown in SEQ ID NO:2; or (d) a polynucleotide comprising the base sequence shown in SEQ ID NO:3 include polynucleotides consisting of a base sequence shown in any one of SEQ ID NO:1, position 337-1878 of SEQ ID NO:1 and SEQ ID NO:3, and a polynucleotide consisting of a base sequence encoding the amino acid sequence shown in SEQ ID NO:2. Further example includes a polynucleotide consisting of a base sequence wherein additional base sequence is added at the 5'- and/or 3'-terminus of the base sequence of SEQ ID NO:1, position 337-1878 of SEQ ID NO:1 or SEQ ID NO:3, or a base sequence encoding the amino acid sequence of SEQ ID NO:2.

The polynucleotide is characterized by that the protein encoded by said polynucleotide has an activity of substantially the same quality as that consisting of the amino acid sequence shown in SEQ ID NO:2. The term "an activity of substantially the same quality" means that a cell expressing the protein encoded by the polynucleotide of the present invention has a characteristic of being recognized by CTLs. Such activity and method of determination are the same as described in "1) The Protein of the Present Invention".

A polynucleotide comprising the base sequence shown in SEQ ID NO: 1 or 3 can be cloned by screening a cDNA library derived from, for example, osteosarcoma cell lines such as SaOS-2 using an appropriate portion of the base sequence disclosed in GenBank Accession No. AF263928 or the one herein disclosed in SEQ ID NO: 1 or 3 as a probe for hybridization or a primer for PCR. One ordinary skilled in the art can easily conduct the cloning according to the method described in Molecular Cloning 2nd Edt. Cold Spring Harbor Laboratory Press (1989), etc.

Examples of a polynucleotide comprising substantially the same base sequence as any one of polynucleotides (a) to (d) above specifically include the followings:

(e) a polynucleotide capable of hybridizing to a complementary strand of any one of polynucleotides (a) to (d) under stringent conditions, and being characterized by that a cell expressing a protein encoded by the polynucleotide is recognized by CTLs;

(f) a polynucleotide comprising a base sequence having at least 70% sequence identity with a polynucleotide set forth in any one of (a) to (d) above, and being characterized by that a cell expressing a protein encoded by the polynucleotide is recognized by CTLs; and (g) a polynucleotide encoding a protein comprising an amino acid sequence, wherein one or more amino acids are deleted, substituted and/or added in the amino acid sequence encoded by any one of polynucleotides (a) to (d) above, and being characterized by that a cell expressing the protein encoded by the polynucleotide is recognized by CTLs.

Preferred examples include a polynucleotide consisting of substantially the same base sequence as any one of polynucleotides (a) to (d) above. Examples of a polynucleotide consisting of substantially the same base sequence as any one of polynucleotides (a) to (d) above include the polynucleotides (e') to (g) below. (e') a polynucleotide capable of hybridizing to a complementary strand of any one of polynucleotides (a) to (d) above under stringent conditions, and being characterized by that a cell expressing a protein encoded by the polynucleotide is recognized by CTLs;

(f') a polynucleotide comprising a base sequence having at least 70% sequence identity with a polynucleotides set forth in any one of (a) to (d) above, and being characterized by that a cell expressing a protein encoded by the polynucleotide is recognized by CTLs; and (g') a polynucleotide encoding a protein comprising an amino acid sequence, wherein one or more amino acids are deleted, substituted and/or added in the protein encoded by any one of polynucleotides (a) to (d) above, and being characterized by that a cell expressing the protein encoded by the polynucleotide is recognized by CTLs.

Examples of "a polynucleotide capable of hybridizing to a complementary of any one of polynucleotides (a) to (d) above under stringent conditions" include polynucleotides comprising base sequences having at least about 40%, preferably, about 60%, more preferably, about 70%, still more preferably about 80%, further more preferably about 90%, and most preferably, about 95% sequence identity with the base sequence of any one of polynucleotides (a) to (d) above, and specifically, polynucleotides consisting of partial sequences of any one of polynucleotides (a) to (d) above.

Hybridization can be conducted according to a method known per se or a method equivalent thereto, for example, a method described in a fundamental text *Molecular Cloning* 2nd Edt. Cold Spring Harbor Laboratory Press (1989)", and the like. Also, it can be performed using a commercially available library according to the instructions attached thereto.

The "stringent conditions" herein used can be determined on the basis of the melting temperature (Tm) of nucleic acids forming a complex or binding to probe as described in literatures (Berger and Kimmel, 1987, "*Guide to Molecular Cloning Techniques Methods in Enzymology*", Vol. 152, Academic Press, San Diego Calif.; or "*Molecular Cloning*" 2nd Edt. Cold Spring Harbor Laboratory Press (1989)).

For example, hybridization can be carried out in a solution containing 6×SSC (20×SSC means 333 mM sodium citrate, 333 mM NaCl), 0.5% SDS and 50% formamide at 42° C., or in a solution containing 6×SSC (without 50% formamide) at 65° C.

Washing after hybridization can be conducted under a condition around "1×SSC, 0.1% SDS, 37° C.". The complementary strand preferably remains bound to the target sense strand when washed under such washing conditions. More stringent hybridization conditions may involve washing under the conditions of around "0.5×SSC, 0.1% SDS, 42° C." and still more stringent hybridization conditions involve washing conditions of around "0.1×SSC, 0.1% SDS, 65° C.", although it is not limited thereto.

Examples of "a polynucleotide comprising a base sequence having at least 70% sequence identity with a polynucleotides set forth in any one of (a) to (d) above" include polynucleotides comprising base sequences having at least about 70%, preferably, about 80%, more preferably, about 90%, and most preferably, about 95% sequence identity with the base sequence of any one of polynucleotides (a) to (d) above, and specifically, polynucleotides consisting of partial sequences of any one of polynucleotides (a) to (d) above.

The term "sequence identity" herein used refers to the identity and homology between two polynucleotides. The "sequence identity" is determined by comparing two sequences aligned optimally over the regions corresponding to the sequences to be compared. In this context, the both polynucleotides to be compared may have addition or deletion (e.g., "gap") in their sequences for optimum alignment. Such sequence identity can be calculated by preparing alignment using, for example, Vector NTI, ClustalW algorithm (Nucleic Acid Res., 22 (22): 4673-4680(1994)). The sequence identity can be determined using software for sequence analysis, specifically, Vector NTI or GENETYX-MAC, or a sequencing tool provided by a public database.

Polynucleotides having such sequence identity can be prepared according to the aforementioned hybridization method, conventional PCR reaction or reaction for modifying a polynucleotide (deletion, addition or substitution) hereinafter described.

Examples of "a polynucleotide encoding a protein comprising an amino acid sequence, wherein one or more amino acids are deleted, substituted and/or added in the protein encoded by any one of polynucleotides (a) to (d) above" include modified proteins produced artificially or allele variants present in a living body.

In this respect, there is no limitations regarding the number or position of modification (mutation) of amino acid as far as the activity of the protein of the present invention is maintained. Criteria based on which one can determine the number or position of amino acid residue to be deleted, substituted and/or added without reducing the activity can be obtained using a computer program well known in the art, such as DNA Star software. For example, the number of mutation would typically be within 10%, preferably 5% of the total amino acid residues. Furthermore, the amino acid used for substitution preferably has similar characteristics to the one to be substituted in view of retention of structure, which characteristics include polarity, charge, solubility, hydrophobicity, hydrophilicity, amphipathicity, etc. For instance, Ala, Val, Leu, Ile, Pro, Met, Phe and Trp are classified into nonpolar amino acids; Gly, Ser, Thr, Cys, Tyr, Asn and Gln into non-charged amino acids; Asp and Glu into acidic amino acids; and Lys, Arg and His into basic amino acids. One of ordinary skill in the art can select an appropriate amigo acid(s) falling within the same group on the basis of these criteria.

The polynucleotide encoding such protein variants may be prepared by various methods such as site-directed mutagenesis and PCR technique described in *Molecular Cloning*: A Laboratory Manual 2nd Edt. vols. 1-3, Cold Spring Harbor Laboratory Press (1989). It also can be prepared by a known method such as Gapped duplex or Kunkel method using a commercially available kit The polynucleotides of the present invention encode proteins having an activity of substantially the same quality as a protein encoded by the amino acid sequence shown in SEQ ID NO:2. The term "activity of substantially the same quality" refers to the characteristic future that cells expressing a protein encoded by the polynucleotide of the present invention are recognized by CTLs. The said activity and the method of determination are as described in "1) Proteins of the present invention" above.

The nucleic acid comprising the polynucleotide of the present invention may be in either forms of single and double strands. When the polynucleotide of the present invention is double stranded, an expression vector for expressing the protein of the present invention can be constructed by incorporating the above-mentioned polynucleotide into an expression vector. Thus, the nucleic acid of the present invention encompasses an expression vector obtainable by inserting a double strand polynucleotide of the present invention. Thus the present invention encompasses an expression vector constructed by inserting a double strand polynucleotide of the present invention.

An adequate expression vector can be selected depending on the host to be used, purposes, and the like, and include plasmids, phage vectors, virus vectors, etc.

When the host is *Escherichia coli*, examples of vector include plasmid vectors such as pUC118, pUC119, pBR322, pCR3, etc.; and phage vectors such as λZAPII, λgt11, etc. When the host is yeast, examples of vector include pYES2, pYEUra3, etc. When the host is insect cells, vector includes pAcSGHisNT-A, etc. When the host is animal cells, examples of include plasmid vectors such as pCEP4, pKCR, pCDM8, pGL2, pcDNA3.1, pRc/RSV, pRc/CMV, etc; and virus vectors such as retrovirus vector, adenovirus vector, adeno-associated virus vector, etc.

The expression vector may optionally contain a factor(s) such as promoter capable of inducing expression, a gene encoding a signal sequence, a marker gene for selection, terminator, etc.

Furthermore, the expression vector may contain an additional sequence for expressing the protein as a fusion protein with thioredoxin, His tag, GST (glutathione S-transferase), or the like, so as to facilitate the isolation and purification. Vectors usable in such a case include GST fusion protein vectors containing an appropriate promoter (lac, tac, trc, trp, CMV, SV40 early promoter, etc) that functions in host cells, such as pGEX4T; vectors containing Tag sequence (Myc, His, etc) such as pcDNA3.1/Myc-His; and vectors capable of expressing a fusion protein between thioredoxin and His such as pET32a.

Transformed cells containing the vector of the present invention can be prepared by transformant host cells with an expression vector obtained in the above.

Host cells usable herein include Escherichia coli, yeast, insect cells and animal cells. Examples of *Escherichia coli* include strains of *E. coli* K-12 such as HB101, C600, JM109, DH5α and AD494 (DE3). Examples of yeast include *Saccharomyces cerevisiae*. Examples of animal cells include L929, BALB/c3T3, C127, CHO, COS, Vero, Hela and 293-EBNA cells. Examples of insect cells include sf9.

Introduction of an expression vector into host cells can be done using a conventional method suited for the respective host cells above. Specifically, it can be done with calcium phosphate method, DEAE-dextran method, electroporation method, and a method using lipid for gene transfer (Lipofectamine, Lipofectin; Gibco-BRL). Following the introduction, the cells are cultured in a conventional medium containing a selection marker, whereby transformants containing the expression vector can be selected.

The protein of the present invention can be produced by culturing the transformed cells under appropriate conditions, the protein of the present invention can be produced. The resultant protein may be further isolated and purified according to standard biochemical procedures. Thus, purification procedures include salting out, ion exchange chromatography, absorption chromatography, affinity chromatography, gel filtration chromatography, etc. When the protein of the present invention has been expressed as a fusion protein with thioredoxin, His tag, GST, or the like, as mentioned above, the said protein can be isolated and purified by appropriate purification procedures making use of the characteristics of such fusion protein or tags.

Nucleic acids comprising polynucleotides encoding the peptide of the present invention fall within the scope of the nucleic acid of the present invention.

The polynucleotide encoding a peptide of the present invention may be in the form of DNA or RNA. The polynucleotide of the present invention can be easily prepared on the basis of information about the amino acid sequence of the peptide or DNA encoding the same. Specifically, it can be prepared by a conventional method such as DNA synthesis or amplification by PCR.

Specifically, the polynucleotide encoding a peptide of the present invention includes polynucleotides encoding the aforementioned epitope peptides.

The nucleic acid comprising a polynucleotide encoding a peptide of the present invention may be in either form of single- or double-strand. When the polynucleotide of the present invention forms a double strand, an expression vector for expressing the peptide of the present invention (epitope peptide) can be constructed by incorporating the above-mentioned polynucleotide into an expression vector.

The expression vector, host cell, a method for transforming a host cell, and the like herein used are similar to those described above.

4) Inducer of CTL Comprising as an Active Ingredient a Protein of the Present Invention The cell comprising the protein of the present invention has a characteristic of being recognized by CTLs. That is, the protein of the present invention is an inducer of CTL. The so induced CTLs are capable of exhibiting anti-tumor effects through cytotoxic action or production of lymphokines. Accordingly, the protein of the present inventions can be used as an active ingredient of a medicine (cancer vaccine) for treatment or prevention of tumor. The inducer of CTLs comprising a protein of the present invention as an active ingredient exerts therapeutic or preventive effects when administered to a tumor patient in the following manner. The protein, when administered to a tumor patient, is incorporated by antigen-presenting cells and intracellularly degradated; the resultant tumor antigen peptides generated by intracellular degradation bind to HLA antigen to form complexes; the complexes are then presented on the surface of antigen-presenting cells; and CTLs specific for the complex efficiently proliferate in the body and destroy tumor cells. In this way, treatment or prevention of tumors is achieved.

The inducer of CTL comprising as an active ingredient a protein of the present invention can be administered to any tumor patients who are positive for PBF protein shown in SEQ ID NO: 2. Specifically, it can be used for prevention or treatment of all sorts of sarcomas such as osteosarcoma, or a cancer (tumor) such as renal cancer.

The inducer of CTL comprising as an active ingredient a protein of the present invention may be administered together with a pharmaceutically acceptable carrier, for example, an appropriate adjuvant, so that the cellular immunity can be established effectively Examples of adjuvant applicable include those described in a literature (*Clin. Microbiol. Rev.*, 7:277-289, 1994). Specifically, the followings are contemplated: components derived from microorganisms or derivative thereof, cytokines, components derived from plants or derivatives thereof, components derived from marine organisms or derivatives thereof, mineral gels such as aluminium hydroxide, lysolecithin, surfactants such as Pluronic® polyols, polyanion, peptide, oil emulsion (emulsion preparation) and the like. In addition, liposomal preparations, particulate preparations in which the ingredient is bound to beads having a diameter of several μm, preparations in which the ingredient is attached to lipids, microsphere preparations, and microcapsules are also contemplated.

In this context, the "components derived from microorganisms or derivative thereof" can be specifically classified into (a) killed bacteria, (b) Cell Wall Skeleton (hereinafter, "CWS" derived from bacteria), and (c) particular components derived from microorganisms and derivatives thereof.

(a) Examples of killed bacteria include powdery hemolytic streptococcus (e.g., Picibanil®, Chugai Co., Ltd.), cocktail of killed bacterium suspension (e.g., Broncasma Berna®, Sanwa Kagaku Kenkyusho Co., Ltd) or killed bacteria of Mycobacterium tuberculosis, and the like.

(b) Examples of CWS derived from bacteria include CWS from Microbacterium (e.g., Mycobacterium bovis CWS), CWS from Nocardia (e.g., Nocardia rubra CWS), Corynebacterium CWS, etc.

(c) Examples of particular components derived from microorganisms and derivatives thereof include microorganism-derived polysaccharides such as polysaccharides from Mycobacterium tuberculosis (e.g., Ancer®, Zeria Pharmaceutical Co., Ltd.); polysaccharides from Basidiomycetes (Lentinan(V, Ajinomoto, Co., Ltd.,; Krestin®, Sankyo, Co., Ltd.; Basidiomycetes, Coriolus versicolor (Fr) Quel); muramyl dipeptide (MDP) associated compounds; lipopolysaccharides (LPS); lipid A (MPL) associated compounds; glycolipids trehalose dimycolate (TDM); bacterium DNA (e.g., CpG oligonucleotide); and derivatives thereof.

These microorganism-derived components and derivatives thereof can be available from commercial source or can be produced and isolated according to a method described in known literatures (e.g., *Cancer Res.*, 33, 2187-2195 (1973); *J. Natl. Cancer Inst.*, 48, 831-835(1972), *J. Bacteriol.*, 94, 1736-1745 (1967); Gann, 69, 619-626 (1978), *J. Bacteriol.*, 92, 869-879 (1966) or *J. Natl. Cancer Inst.*, 52, 95-101 (1974)).

The term "cytokines", for example, refers to IFN-α, IL-12, GM-CSF, IL-2, IFN-γ, IL-18 or IL-15. These cytokines may be a product of nature or genetic engineering. When a cytokine(s) is commercially available, one can pursue and use the same. Alternatively, cytokines can be prepared recombinantly by cloning a desired gene in a conventional manner on the basis of respective base sequences registered with database such as GenBank, EMBL or DDBJ, ligating the gene into an appropriate expression vector, transforming host cells with the resultant recombinant expression vector, and allowing the cells to express and produce the intended cytokine.

Examples of the "components derived from plants or derivatives thereof" include saponin-derived component Quil A (Accurate Chemical & Scientific Corp), QS-21 (Aquila Biopharmaceuticals Inc.), or glycyrrhizin (SIGMA-ALDRICH, etc.).

Examples of the "components derived from marine organisms or derivatives thereof" include sponge-derived glycolipid α-galactosylceramide.

Examples of oil emulsion (emulsion preparation) include emulsion preparations of water-in-oil type (w/o), oil-in-water type (o/w) and water-in-oil-in-water type (w/o/w). In the water-in-oil type (w/o) emulsion preparation, an active ingredient is dispersed in water as the disperse phase. In the oil-in-water type (o/w) emulsion preparation, an active ingredient is dispersed in water as the disperse medium. Further, in the water-in-oil-in-water type (w/o/w) emulsion preparation, an active ingredient is dispersed in water as the most internal phase. Such emulsion preparations can be produced in accordance with the teaching in, for example, JP-A-8-985, JP-A-9-122476, or the like.

The "liposomal preparations" refer to microparticles wherein an active ingredient in water phase or membrane is encapsulated with liposomes of lipid bilayer structure. Major lipids for preparation of liposomes include phosphatidyl choline, sphingomyelin, etc. Dicetyl phosphate, phosphatidic acid, phosphatidyl serine or the like that confers charge may also be added for stabilization of liposomes. The method of producing liposomes include ultrasonic method, ethanol injection method, ether injection method, reverse phase evaporation method, French press extraction method, and the like.

The "microsphere preparations" refer to microparticles composed of a homogeneous polymer matrix wherein an active ingredient is dispersed in said matrix. The matrix can be composed of a biodegradable polymer such as albumin, gelatin, chitin, chitosan, starch, polylactic acid, polyalkyl cyanoacrylate, and the like. The microsphere preparations can be prepared by any of known methods without limitation, including those described in literatures (*Eur. J. Pharm. Biopharn.* 50:129-146, 2000; *Dev. Biol. Stand.* 92:63-78, 1998; *Pharm. Biotechnol.* 10:1-43, 1997, etc.).

The "microcapsule preparations" refer to microparticles containing an active ingredient as a core substance which is enveloped with a film. The coating material used for film includes a film-forming polymer such as carboxymethylcellulose, cellulose acetate phthalate, ethyl cellulose, gelatin, gelatin/acacia, nitrocellulose, polyvinyl alcohol, hydroxypropyl cellulose, and the like. The microcapsule preparations can be prepared by coacervation method, surface polymerization, and the like.

Administration may be achieved, for example, intradermally, subcutaneously, intramuscularly, or intravenously. Although the dosage of the protein of the present invention in the formulation to be administered may be adjusted as appropriate depending on, for example, the disease to be treated, the age and the body weight of the patient, it is usually within the range of 0.0001-1000 mg, preferably, 0.001-100 mg, more preferably 0.01-10 mg, which can be administered once in every several days to every several months.

5) Inducer of CTL Comprising as an Active Ingredient a Pentide of the Present Invention The peptide of the present invention is an inducer of CTL having an activity of inducing CTLs. The so induced CTLs can exert the anti-tumor effects through cytotoxic action or production of lymphokines. Accordingly, the peptide of the present invention can be used as an active ingredient of a medicine for treatment or prevention of tumor. When an inducer of CTL comprising as an active ingredient the peptide of the present invention is administered to a tumor patient, the peptide of the present invention is presented to an HLA antigen in antigen-presenting cells. Then, CTLs specific for the presented binding complex between the HLA antigen and the peptide of the present invention proliferate, which in turn destroy tumor cells. In this way, the treatment or prevention of tumors in a patient can be achieved.

The inducer of CTL comprising as an active ingredient a peptide of the present invention can be administered to any tumor patients who are positive for PBF protein shown in SEQ ID NO: 2. Specifically, it can be used for prevention or treatment of all sorts of sarcomas such as osteosarcoma, or a cancer (tumor) such as renal cancer.

The inducer of the present invention may comprise a single CTL epitope (peptide of the present invention) or a epitope peptide wherein the said peptide is ligated with other peptide(s) (CTL epitope or helper epitope) as an active ingredient. Recently, an epitope peptide composed of multiple (plural) CTL epitopes (antigen peptides) linked together has been shown to have an activity of inducing CTLs efficiently For example, it has been reported that about 30-mer epitope peptide wherein CTL epitopes restricted to HLA-A2-, -A3,- - A11 or B53 originated from tumor antigen protein PSA are ligated induced CTLs specific for respective CTL epitopes (*Journal of Immunology* 1998, 161: 3186-3194). In addition, it has been reported that an epitope peptide wherein a CTL epitope(s) and a helper epitope(s) are ligated can induce CTLs efficiently. When the peptide of the present invention is administered in the form of epitope peptide, the said peptide is incorporated by antigen-presenting cells; respective antigen peptides generated by intracellular degradation bind to an HLA antigen to form complexes; the complexes are presented on the surface of antigen-presenting cells in high density; CTLs specific for the complexes efficiently proliferate in the body, and destroy tumor cells. In this way, treatment or prevention of tumors is achieved.

The inducer of CTL comprising as an active ingredient a protein of the present invention may be administered together with a pharmaceutically acceptable carrier, for example, an appropriate adjuvant, so that the cellular immunity can be established effectively Examples of adjuvant applicable include those described in a literature (*Clin. Microbiol. Rev.*, 7:277-289, 1994). Specifically, the followings are contemplated: components derived from microorganisms or a derivative thereof, cytokines, components derived from plants or derivatives thereof, components derived from marine organisms or derivatives thereof, mineral gels such as aluminium hydroxide, surfactants such as lysolecithin, Pluronic® polyols, polyanion, peptide, oil emulsion (emulsion preparation) and the like. In addition, liposomal preparations, particulate preparations in which the ingredient is bound to beads having a diameter of several μm, preparations in which the ingredient is attached to lipids, microsphere preparations, and microcapsules are also contemplated. Concrete examples of these adjuvants are the same as those descried in the above "4) CTL inducers comprising a protein of the present invention".

Administration may be achieved, for example, intradermally, subcutaneously, intramuscularly, or intravenously. Although the dosage of the protein of the present invention in the formulation to be administered may be adjusted as appropriate depending on, for example, the disease to be treated, the age and the body weight of the patient, it is usually within the range of 0.0001-1000 mg, preferably 0.001-1000 mg, more preferably 0.1-10 mg, which can be administered once in every several days to every several months.

6) Inducer of CTL Comprising as an Active Ingredient a Nucleic Acid of the Present Invention The cells expressing the nucleic acid of the present invention has a characteristic of being recognized by CTLs. Accordingly, the nucleic acid of the present invention is an inducer of CTLs. The so induced CTLs can exert the antitumor effects through cytotoxic action or production of lymphokines. The nucleic acid of the present invention therefore can be used as an active ingredient of a medicine for treatment or prevention of tumor. The inducer comprising as an active ingredient the nucleic acid of the present invention, when administered, can exert therapeutic or preventive effects on tumors through the expression of the nucleic acid.

For example, the nucleic acid of the present invention incorporated into an expression vector is administered to a tumor patient in the following manner, tumor antigen proteins are highly expressed in antigen-presenting cells. Thereafter, tumor antigen peptides generated by intracellular degradation form complexes with HLA antigen; the complexes are then presented on the surface of antigen-presenting cells in high density; and tumor-specific CTLs proliferate in the body efficiently and destroy tumor cells. In this way, treatment or prevention of tumors is achieved.

The inducer of CTL comprising as an active ingredient a nucleic acid of the present invention can be administered to any tumor patients who are positive for PBF gene shown in SEQ ID NO: 1 and for PBF that is an expression product of said gene. Specifically, it can be used for prevention or treatment of all sorts of sarcomas such as osteosarcoma, or a cancer such as renal cancer Administration and introduction of the nucleic acid of the present invention into cells may be achieved using viral vectors or according to any one of other procedures (*Nikkei-Science*, April, 1994, pp. 20-45; *Gekkan-Yakuji*, 36(1), 23-48 (1994); *Jikken-Igaku-Zokan*, 12(15), 1994, and references cited therein).

Examples of a method for introduction with viral vectors comprises incorporating DNA of the present invention into DNA or RNA virus such as retrovirus, adenovirus, adeno-associated virus, herpesvirus, vaccinia virus, poxvirus, poliovirus, or Sindbis virus, and introducing into cells. Above all, a method that uses retrovirus, adenovirus, adeno-associated virus, or vaccinia virus is particularly preferred.

Examples of other methods include a method wherein an expression plasmid is directly injected intramuscularly (DNA vaccination), liposome method, Lipofectin method, microinjection, calcium phosphate method and electroporation. DNA vaccination and liposome method are particularly preferred.

Regarding method to make a nucleic acid of the present invention act as a medicament in practice, there are in vivo method wherein the nucleic acid is directly introduced into the body, and ex vivo method wherein the nucleic acid is introduced extracorporeally into a certain cells removed from human, and the cells are reintroduced into the body (Nikkei-Science, April, 1994, pp. 20-45; Gekkan-Yakuji, 36(1), 23-48 (1994); Jikkenn-Igaku-Zokan, 12(15), 1994; and references cited therein). An in vivo method is more preferred.

In case of in vivo method, the administration can be effected through any appropriate routes depending on the disease and symptom to be treated and other factors. For example, it may be administered via intravenous, intraarterial, subcutaneous, intracutaneous, intramuscular route, or the like. When the administration is carried out by in vivo method, the compositions may be administered in various forms such as solution, and are typically formulated, for example, in the form of injection containing the nucleic acid of the present invention as an active ingredient, to which conventional carriers may also be added, if necessary. As for the liposomes or membrane-fused liposomes (such as Sendai virus (HVJ)-liposomes) containing the nucleic acid of the present invention, they may be in the form of liposomal formulation such as suspension, frozen drug, centrifugally-concentrated frozen drug, or the like.

Although the dosage of the nucleic acid of the present invention in the formulation to be administered may be adjusted as appropriate depending on, for example, the disease to be treated, the age and the body weight of the patient, it is usually, as the amount of nucleotide in the nucleic acid, within the range of 0.0001-100 mg, preferably, 0.001-10 mg, which can be administered once in every several days to every several months.

Recently, a polynucleotide encoding an epitope peptide wherein multiple (plural) CTL epitopes (antigen peptides) are ligated or wherein a CTL epitope(s) and a helper epitope(s) are ligated has been shown to induce CTLs in vivo efficiently For example, it is reported that a DNA (minigene) encoding an epitope peptide wherein HBV-originated HLA-A2-restricted tumor antigen peptides (6 peptides), HLA-A11-restricted tumor antigen peptides (3 peptides) and a helper epitope are ligated induced in vivo CTLs directed to the respective epitopes efficiently (*Journal of Immunology* 1999, 162: 3915-3925).

Accordingly, a polynucleotide prepared by ligating one or more polynucleotides encoding the peptide of the present invention, optionally in association with another polynucleotide(s) encoding different peptide(s) can be used as an active ingredient after introducing into an appropriate expression vector. Such an inducer of CTL may be applied to the same administration manner or form that described above.

7) Antigen-Presenting Cells of the Present Invention

The tumor antigen protein, peptide and nucleic acid of the present invention may also be used in vitro for treatment of tumor patients as follows. That is, the antigen-presenting cells can be prepared by bringing a cell having antigen-presenting ability into contact with any one of proteins, peptides and nucleic acids of the present invention in vitro. Specifically, the present invention provides an antigen-presenting cell presenting a complex between an HLA antigen and any one of proteins, peptides and nucleic acids of the present invention, which cell has been prepared by bringing a cell having antigen-presenting ability isolated from a tumor patient with any one of proteins, peptides and nucleic acids of the present invention in vitro, and a method for preparing the same.

In this context, the "cells having antigen-presenting ability" are not limited to particular cells and may be any cells that express on the surface an HLA antigen capable of presenting the peptide of the present invention; however, dendritic cells known to have especially high antigen-presenting ability are preferred.

Further, the substance used for preparing the antigen-presenting cells of the present invention from cells having antigen-presenting ability may be any of proteins, peptides and nucleic acids of the present invention.

The antigen-presenting cells of the present invention can be prepared by isolating from a tumor patient cells having antigen-presenting ability, pulsing the cells in vitro with a protein or peptide of the present invention, and allowing the cells to present a complex between an HLA antigen and a peptide of the present invention (Cancer Immunol. Immunother., 46: 82, 1998; *J. Immunol.* 158: p1796, 1997; *Cancer Res.*, 59:1184, 1999). When dendritic cells are used, antigen-presenting cells of the present invention may be prepared, for example, by isolating lymphocytes from peripheral blood of a tumor patient using Ficoll method, removing non-adherent cells, incubating the adherent cells in the presence of GM-CSF and IL-4 to induce dendritic cells, and incubating and pulsing said dendritic cells with a protein or a peptide of the present invention.

When antigen-presenting cells of the present invention are prepared by introducing a nucleic acid of the present invention into the aforementioned cells having an antigen-presenting ability, said nucleic acid may be in the form of DNA or RNA. In particular, DNA may be used according to the teaching in *Cancer Res.*, 56:5672, 1996 or *J. Immunol.*, 161: p5607, 1998, and RNA according to the teaching in *J. Exp. Med.*, 184:p465, 1996, for example.

The aforementioned antigen-presenting cells can be used as an active ingredient of an inducer of CTL. The inducer of CTL comprising as an active ingredient the said antigen-presenting cells preferably contains physiological saline, phosphate buffered saline (PBS), medium, or the like to stably maintain the antigen-presenting cells. It may be administered, for example, intravenously, subcutaneously, or intradermally. Reintroduction of an inducer of CTL comprising as an active ingredient antigen-presenting cells as an active ingredient into a PBF-positive patient brings about efficient induction of specific CTLs in the body of said patient, and, as a result, treatment of tumor.

8) CTLs of the Present Invention

The protein, peptide and the nucleic acid of the present invention can be used in vitro in treatment of tumor patients in the following manner. That is, any one of protein, peptide and the nucleic acid of the present invention can be used to induce CTLs in vitro by bringing the same into contact with peripheral lymphocytes. Specifically, the present invention provides a CTL induced by bringing peripheral blood lymphocytes from a tumor patient into contact in vitro with any one of protein, peptide and nucleic acid of the present invention and the method of induction of CTL.

For melanomas, therapeutic effect has been observed in adoptive immunotherapy wherein tumor-infiltrating T cells are removed from a patient, cultured ex vivo in large quantities and returned into the same patient (*J. Natl. Cancer. Inst.*, 86: 1159, 1994). Further, in mouse melanoma, suppression of metastasis has been observed in treatment wherein splenocytes were stimulated with tumor antigen peptide TRP-2 in vitro thereby making CTLs specific for the tumor antigen peptide to proliferate, and the CTLs are administered to a melanoma-grafted mouse (*J. Exp. Med.*, 185:453, 1997). This resulted from in vitro proliferation of CTLs that specifically recognize the complex between an HLA antigen of antigen-presenting cells and the tumor antigen peptide. Accordingly, a therapeutic method comprising stimulating in vitro peripheral blood lymphocytes from a patient with a protein, peptide or nucleic acid of the present invention to proliferate tumor-specific CTLs, and returning the CTLs into the patient is believed to be effective.

The CTLs can be used as an active ingredient of a therapeutic or preventive agent for tumor. Said therapeutic or preventive agent preferably contains physiological saline, phosphate buffered saline (PBS), medium, or the like to stably maintain CTLs. It may be administered, for example, intravenously, subcutaneously or intradermally. By returning a therapeutic or preventive agent comprising as an active ingredient the CTLs into a patient positive for PBF of the present invention, the cytotoxic action of CTLs is enhanced in the body of patient and whereby the tumor cells are killed and treatment of tumor is achieved.

9) Antibody Against the Peptide of the Present Invention

The present invention provides antibody capable of specifically binding to the peptide of the present invention. The antibody of the present invention may be in the form of, although it is not limited to, polyclonal or monoclonal antibody raised against a peptide of the present invention. Although there are no limitations regarding the antibody of the present invention subject that it specifically binds to the peptide of the present invention, concrete examples include antibodies that specifically bind to a tumor antigen peptide consisting of an amino acid sequence of any one of those described in SEQ ID NO:6-55.

Preparation of antibodies is well known in the art and the antibodies of the present invention can be prepared according to any one of these conventional methods (Current protocols in Molecular Biology edit. Ausubel et al. (1987) Publish. John Wiley and Sons. Section 11.12-11.13, Antibodies; A Laboratory Manual, Lane, H, D. et al., ed., Cold Spring Harbor Laboratory Press, New York 1989).

Specifically, when the antibodies of the present invention are polyclonal, they can be obtained by immunizing non-human animal such as rabbit using a peptide of the present invention (e.g., a tumor antigen peptide consisting of amino acid sequence shown in any one of SEQ ID NO: 6-55) as an antigen, and recovering the antibodies from serum of the immunized animal in a conventional manner. In the case of monoclonal antibodies, they can be obtained by immunizing non-human animal such as mouse with a peptide of the present invention (e.g., a tumor antigen peptide consisting of amino acid sequence shown in any one of SEQ ID NO: 6-55), subjecting the resultant splenocytes to cell fusion with myeloma cells, and recovering antibodies from hybridoma cells (Current protocols in Molecular Biology edit. Ausubel et al. (1987) Publish. John Wiley and Sons. Section 11.4-11.11).

The antibodies against the peptide of the present invention can also be produced while enhancing the immunological response using different adjuvants depending on the host. Examples of adjuvants include Freund adjuvants; mineral gels such as aluminium hydroxide; surfactants such as lysolecithin, Pluronic® polyol, polyanion, peptide, oil emulsion, keyhole limpet hemocyanin and dinitorophenol; human adjuvants such as BCG (Bacille de Calmette-Guerin) or Corynebacterium, etc.

As mentioned above, antibodies that recognize a peptide of the present invention and antibodies that neutralize activity thereof may easily be prepared by immunizing an animal in a conventional manner. The antibodies may be used in affinity chromatography, immunological diagnostic method, and the like. Immunological diagnostic method may be selected as appropriate from immunoblotting, radioimmunoassay (RIA), enzyme-linked immunosorbent assay (ELISA), a fluorescent or luminescent assay, and the like. The immunological diagnostic method would be effective for diagnosing cancers expressing the PBF gene of the present invention, such as sarcomas and renal cancers.

10) Tumor Marker 10-1) Tumor Marker Related to Polynucleotide of the Present Invention The present inventors have found that PBF gene defined in SEQ ID NO: 1 is highly expressed specifically in sarcomas and renal cancers compared to normal cells. Accordingly, the presence or absence of a tumor especially sarcoma or renal and the degree thereof can be specifically detected by examining the presence or extent of expression of the gene, which in turn allows the diagnostic method of such diseases.

Accordingly, the polynucleotide of the present invention is useful as a tool (tumor marker) for diagnosing whether or not a test subject is suffering from a tumor, or degree of the disease, wherein the presence/absence or extent of expression of PBF gene above in a test subject is detected using the polynucleotide.

The tumor marker of the present invention is characterized by that it comprises at least 15 contiguous nucleotides in the base sequence of aforementioned polynucleotide of the present invention, which encodes a protein comprising the same or substantially the same amino acid sequence as that shown in SEQ ID NO: 2.

Specifically, the tumor marker of the present invention includes a polynucleotide and/or a complementary polynucleotide thereof, which polynucleotide comprises at least 15 contiguous nucleotides in the base sequence of SEQ ID NO 1 or SEQ ID NO: 3.

In this context, the term "complementary polynucleotide (complementary strand, reverse strand (antisense strand)" refers to a polynucleotide which is in complementary relation in regard to bases (e.g., A:T, G:C) in the full- or partial-sequence (hereinafter, said sequence may be referred to as "positive strand (sense strand)" for convenience) of the polynucleotide consisting of the base sequence shown in SEQ ID NO: 1 or 3, which partial sequence comprises at least 15 contiguous bases. The "complementary strand" includes both a sequence forming completely complementary strands with the base sequence of target positive strand and a sequence being complementary enough to hybridize with the base sequence of target positive strand under stringent conditions. The stringent conditions herein used can be determined on the basis of the melting temperature (Tm) of nucleic acids forming a complex or binding to probe as described in literatures (Berger and Kimmel, 1987, "Guide to Molecular Cloning Techniques Methods in Enzymology", Vol. 152, Academic Press, San Diego Calif.). For example, washing after hybridization can be conducted under a condition around "1×SSC, 0.1% SDS, 37° C. in usual. The complementary strand preferably remains bound to the target sense strand when washed under such washing conditions. More stringent hybridization conditions may involve washing under the conditions of around "0.5×SSC, 0.1% SDS, 42° C." and still more stringent hybridization conditions involve washing conditions of around "0.1×SSC, 0.1% SDS, 65° C.", although it is not limited thereto. Such complementary strand include specifically, for example, a strand consisting of a base sequence having complete complementarity, a homology of at least 90%, or preferably at least 95% in relation to the base sequence of a target positive strand.

The polynucleotide of the positive strand may include not only those comprising the full or a partial sequence of the base sequence shown in SEQ ID NO: 1 or 3, but also those being in a complementary relation with the base sequence of above-mentioned complementary strand.

Furthermore, the above-mentioned polynucleotides of positive or negative (reverse) strands can be used as a tumor marker in the form of single strand as well as double strand.

As a concrete example, the tumor marker of the present invention may be a polynucleotide consisting of a base sequence (full sequence) shown in SEQ ID NO: 1 or 3, or a polynucleotide comprising a complementary strand thereof. It may be a polynucleotide consisting of a partial sequence of the above-mentioned full sequence or its complementary sequence as long as said polynucleotide selectively (specifically) recognizes the gene of the present invention or a polynucleotide originated therefrom. The partial sequence includes a polynucleotide comprising a sequence comprising at least contiguous 15 bases selected arbitrarily from the base sequence of the aforementioned full sequence or a complementary sequence thereof.

The term "selectively (specifically) recognizes" used herein means that, in the case of Northern blotting, the PBF gene or a polynucleotide derived therefrom of the present invention can be specifically detected, and in the case of RT-PCR method, the PBF gene or a polynucleotide derived therefrom of the present invention can be specifically generated. However, the above definition is not restrictive and any criteria can be used as long as one ordinary skilled in the art can determine that the detected substances or products above are originated from PBF gene.

For example, the tumor marker of the present invention can be designed on the basis of the base sequence shown in SEQ ID NO: 1 or 3 by means of primer 3 or a vector NTI (Infomax). Specifically, a candidate sequence for primer or probe, or a sequence at least comprising said sequence as a partial sequence can be used as a primer or probe, which candidate sequence is obtainable by subjecting the base sequence of the gene of the present invention to primer 3 or vector NTI software. Example of such a tumor marker of the present invention includes a primer shown in SEQ ID NO: 4 or 5.

The tumor marker of the present invention may be at least 15 bases in length; however, depending on the use of the marker, the length can be appropriately selected and designated.

In the present invention, the detection (diagnostic method) of tumors is conducted by assessing the presence/absence or the level (amount of products) of expression of PBF gene in a biopsy tissue especially sample from sarcoma or renal cancer of a patient suspected to be affected by tumor. In this case, the aforementioned tumor marker of the present invention may serve as a primer that specifically recognizes and brings about proliferation of an RNA resulted from the expression of PBF gene or a polynucleotide derived therefrom, or as a probe for detecting specifically said RNA or a polypeptide derived therefrom.

The tumor makers of the present invention may include, when used as a primer in the detection of tumors, those comprising a base sequence of, in general, 15-100 bp, preferably 15-50 bp, more preferably 15-35 bp in length. When used as a detection probe, the tumor markers may, in general, comprise a base sequence of from 15 bp to 1 kp, preferably from 100 bp to 1 kb.

The tumor marker of the present invention can be used as a primer or a probe in a conventional manner in any of known methods for detecting specifically a particular gene such as Northern blotting, RT-PCR, in situ hybridization, and the like.

The tumor marker of the present invention is useful in the diagnostic method or detection of tumor, that is, diagnostic method of presence/absence or pathology, or the extent thereof. Specifically, diagnostic method with the tumor marker can be conducted by comparing the expression level of PBF gene in biopsy tissue suspected to be affected by tumor of a test subject and that in a similar tissue of a normal subject. In this case, the "difference in expression level" refers not only the presence/absence of expression, but also the expression differential is at least 2-fold, preferably 3-fold, when expression is observed in tissues of both groups. Specifically, since the expression of PBF gene is induced in tumors, a test subject is suspected to be affected by tumor, if the expression in a tissue sample of the test subject is at least 2-fold, preferably 3-fold higher compared to that in the corresponding tissue of a normal subject.

10-2) Tumor Marker Related to Antibody of the Present Invention

The present invention provides an antibody capable of specifically recognizing a protein of the present invention or partial peptides thereof (including the peptides of the present invention) as a tumor marker. More specifically, the present invention provides a tumor marker comprising an antibody capable of specifically recognizing a protein of the present invention consisting of the amino acid sequence shown in SEQ ID NO: 2 or partial peptides thereof (including the peptides of the present invention) as a tumor marker.

The present inventors have found that the PBF gene of the present invention is highly expressed in diverse sarcomas and renal cancers. Accordingly, the presence/absence of the tumor above (sarcoma, renal cancer, etc.) or the extent thereof can be detected specifically by detecting the presence/absence of expression products of said gene or extent of expression, whereby such diseases can diagnosed.

Accordingly, the antibody above is useful as a tool (tumor marker) for diagnosing whether or not a test subject is suffering from a tumor, or degree of the disease, wherein the presence/absence or extent of expression of the protein above in a test subject is detected using the antibody.

The antibody of the present invention is not restricted to any form and includes polyclonal or monoclonal antibody raised against a protein of the present invention as an immunogen, specifically, PBF protein consisting of the amino acid sequence shown in SEQ ID NO: 2. The antibody of the present invention also includes those having ability to bind to polypeptides consisting of generally 8, preferably 15, more preferably 22 contiguous amino acids in the protein of the present invention.

Preparation of antibodies is well known in the art and the antibodies of the present invention can be prepared according to any one of these conventional methods (Current protocols in Molecular Biology, Chapter 11.12-11.13(2000))

Specifically, when the antibodies of the present invention are polyclonal, they can be obtained by immunizing non-human animal such as rabbit with a protein of the present invention that has been expressed in $E.\ coli$ and purified in a conventional manner, or a synthetic oligopeptide comprising a partial amino acid sequence of said protein of the present invention, and recovering the antibodies from serum of the immunized animal in a conventional manner. In the case of monoclonal antibodies, they can be obtained by immunizing non-human animal such as mouse with a protein of the present invention that has been expressed in $E.\ coli$ and purified in a conventional manner, or a synthetic oligopeptide comprising a partial amino acid sequence of said protein of the present invention, subjecting the resultant splenocytes to cell fusion with myeloma cells, and recovering antibodies from hybridoma cells (Current protocols in Molecular Biology edit. Ausubel et al. (1987) Publish. John Wiley and Sons. Section 11.4-11.11).

The protein of the present invention used as an immunogen in the preparation of antibody of the present invention (specifically, PBF protein consisting of amino acid sequence shown in SEQ ID NO:2) is obtainable by processes comprising cloning of a DNA on the basis of information herein provided (SEQ ID NO: 1, 3), construction of plasmid, transfection into a host cell, incubation of host cells, and recovery of protein from cultured medium. These processes can be conducted by any one of methods known to those skilled in the art or described in a literature (*Molecular Cloning*, T. Maniatis et al., CSH Laboratory (1983), DNA Cloning, DM. Glover, IRL PRESS (1985)), and the like. The partial peptides of the protein of the present invention can also be produced by a usual method for chemical synthesis (peptide synthesis) on the basis of information regarding amino acid sequence (SEQ ID NO:2) herein provided. The detail thereof is described above in 1) to 3).

The antibody of the present invention may be the one obtainable using an oligopeptide comprising a partial amino acid sequence of the protein of the present invention. An oligo(poly)peptides used in the preparation of antibodies does not needed to possess a functional biological activity;

however, it is desired that such a peptide possesses a similar immunogenicity to the protein of the present invention. Preferred examples include oligo(poly)nucleotides having said immunogenicity and comprising at least 8, preferably 15, more preferably 20 contiguous amino acids in the amino acid sequence of the protein of the present invention.

The production of antibodies against an oligo(poly)peptide can also be carried out while administering to the host various adjuvants so as to enhance the immunoreactivity. Such adjuvants (but are not limited thereto) include Freund adjuvants; mineral gels such as aluminium hydroxide; surfactants such as lysolecithin, Pluronic( polyol, polyanion, peptide, oil emulsion, keyhole limpet hemocyanin and dinitorophenol; human adjuvants such as BCG (Bacille de Calmette-Guerin) or Corynebacterium, etc.

The antibody of the present invention has a characteristic of specifically binding to PBF protein, and hence makes it possible to detect specifically the above-mentioned protein expressed in tissues of a test subject. Thus, the said antibody is useful as a probe for detecting the presence/absence of expression of PBF in tissues of a test subject.

Specifically, PBF can be detected by obtaining a sample from a tissue or blood suspected to be affected by biopsy or the like, preparing a protein therefrom in a conventional manner, and conducting detection by a known method such as Western blotting, ELISA, or the like using the antibody as a probe.

Diagnostic method of tumors may be accomplished by determining the difference in the quantity of PBF proteins in a tissue of test subject and that in the corresponding normal tissue. In this case, the quantitative difference of protein may involve the cases where the protein is either present or absent, and the amount of protein differs at least by 2-fold, preferably 3-fold. Specifically, since the expression of PBF gene is induced in tumors (sarcoma, renal cancer), a test subject is suspected to be affected by tumor, if a tissue of said test subject contains the expression product (PBF) of the gene and the quantity of PBF therein is at least 2-fold preferably 3-fold larger than that in the normal tissue.

10-3) Tumor Marker Related to Protein or Peptide of the Present Invention

The present invention provides, as a tumor marker, a protein or a peptide capable of specifically recognizing an antibody against the protein of the present invention or a partial peptide thereof. More specifically, the present invention provides a tumor marker comprising the protein consisting of amino acid sequence shown in SEQ ID NO: 2 or a partial peptide thereof of the present invention.

Examples of the partial peptide of the protein of the present invention that serves as a component of tumor markers include polypeptides consisting of at least 8, preferably 15, and more preferably 20 contiguous amino acids in the amino acid sequence of the protein of the present invention. Tumor can be diagnosed by detecting an antibody in a sample (e.g., blood, tissue suspected to contain tumor) using a protein or a peptide (polypeptide) of the present invention as a diagnostic agent. The method for preparing the protein of the present invention and peptides are as described in 1) and 2) above.

Specifically, an antibody against PBF can be detected by collecting blood or obtaining a tissue sample suspected to be affected by biopsy or the like, preparing a protein therefrom in a conventional manner, and conducting detection by a known method such as Western blotting, ELISA, or the like using the protein of the present invention or a peptide above as a probe.

Diagnostic method of tumor can be done by determining the difference between the amount of anti-PBF antibody and that in the corresponding normal tissue. The difference in the amount of protein includes the cases where the protein is present or absent, and the quantity of protein differs by at least 2-fold, preferably 3-fold. Specifically, since the expression of PBF gene is induced in tumors (sarcomas, renal cancer), a test subject is suspected to be affected by tumor, if a tissue of the test subject contains antibodies against the expression products (PBF) of said gene and the quantity of said anti-PBF antibody is determined to be at least 2-fold more preferably 3-fold compared to that in normal tissue.

10-4) Tumor Marker Related to HLA Tetramer

The present invention also provides an HLA tetramer comprising a peptide of the present invention and an HLA antigen, and a tumor marker comprising the said HLA tetramer.

The term "HLA tetramer" herein used means a tetramer wherein biotinilated HLA monomers, which monomer is a complex formed by association of α-chain of HLA antigen and β 2 microglobulin with a peptide (antigen peptide), are allowed to bind to avidin so as to form a tetramer (Science 279: 2103-2106 (1998); Science 274: 94-96 (1996)). At present, HLA tetramers comprising a variety of antigen peptides are commercially available (e.g., Hayashibara Biochemical Laboratories, Inc.), and tetramers comprising a peptide of the present invention and an HLA antigen can easily be prepared.

Examples of specific tetramers include tetramers comprising an antigen peptide consisting of an amino acid sequence shown in any one of SEQ ID NO: 6-45 and HLA-A24 antigen, and tetramers comprising an antigen peptide consisting of an amino acid sequence shown in any one of SEQ ID NO: 46-55 and HLA-B55 antigen.

The HLA tetramers are preferably fluorescently labeled so as to facilitate the selection or detection of bound CTLs by a know detection method such as flow cytometry, fluorescence microscope, or the like. Specifically, tetramers can be labeled with, for example, phycoerythrin (PE), fluoresce in isothiocyanates (FITC), pyridazine chlorophyll protein (Percy), or the like.

HLA-A24 antigen (α-chain of HLA-A24 antigen) as a component of HLA tetramers can readily be cloned by a conventional method such as PCR on the basis of known base sequence of HLA-A2402 gene that is disclosed in *Cancer Res.*, 55: 4248-4252 (1995) and Genbank Accession No. M64740. Also, HLA-B55 antigen can be cloned on the basis of known base sequence of HLA-B5502 gene (GenBank Acc. No. M77777, *J. Immunol.*, 148(4), 1155-1162(1992)).

It is preferred that β2 microglobulin, a component of tetramers, is human β2 microglobulin. Said human β2 microglobulin can readily be cloned by a conventional method such as PCR on the basis of known base sequence of human β2 microglobulin (GenBank Acc. No. AB021288).

Process for preparing HLA tetramers comprising the above components of HLA tetramers is well known in the art (e.g., Science 279: 2103-2106 (1998); Science 274: 94-96 (1996), etc.). The preparation will be hereinafter described briefly taking HLA-A24 antigen as an example.

First, both expression vectors each containing HLA-A24 α-chain and β2 microglobulin are introduced into *E. coli* or mammalian cells capable of expressing a protein, and the cells are cultured for expression. For this step, *E. coli* (e.g. BL21) is preferred. The resultant monomer HLA-A24 complex and a peptide of the present invention are mixed to form a soluble HLA-peptide complex. The HLA-peptide complex is biotinylated with BirA enzyme at the C-terminal sequence of HLA-A24 α-chain. When the biotinylated HLA-peptide complex is mixed with fluorescently labeled avidin at molar ratio of 4:1, HLA tetramers are formed. It is preferred to conduct gel filtration for purifying protein in each step above.

10-5) Detection Method for Tumor (Diagnostic Method)

The present invention provides a detection method for tumors (diagnostic method) utilizing the aforementioned tumor marker of the present invention.

Specifically, the detection method (diagnostic method) of the present invention comprises collecting blood from a test subject or isolating a specimen by biopsy or the like from his/her tissue suspected to be affected; detecting and measuring the expression level of PBF gene, quantity of PBF protein encoded by the gene, quantity of antibody against said PBF protein, or quantity of CTL capable of recognizing a complex between HLA antigen and tumor antigen peptide from said PBF protein; and evaluating whether or not the test subject has a tumor such as sarcoma, renal cancer, or the like, on the basis of the measurements. In addition, according to the detection method (diagnostic method) of the present invention, it is possible to detect (diagnose) whether a therapeutic agent administered to a tumor patient for amelioration of the tumor can actually bring about improvement of disease or not, or the extent of improvement. Furthermore, the detection method (diagnostic method) of the present invention can be used for selecting tumor patients possibly adaptable to a medicine comprising as an active ingredient a protein, peptide or nucleic acid of the present invention, or the evaluation of the therapeutic effect of said medicine.

The detection method of the present invention comprises the following steps (a), (b) and (c):

(a) bringing a sample from living body of the test subject into contact with a tumor marker of the present invention;

b) measuring expression level of PBF gene, quantity of PBF protein, quantity of anti-PBF antibody, or quantity of CLT capable of recognizing a complex between tumor antigen peptide from PBF and HLA antigen in the sample, and (c) evaluating whether or not the test subject has a tumor on the basis of measurements in (b).

The sample from a living body herein used includes a sample that can be prepared from tissues such as a tissue suspected to contain tumor, surrounding tissues, or blood, of a living body of test subject. Specifically, such sample includes (i) RNA-containing sample that can be prepared from the above tissue, (ii) polynucleotide-containing sample that can further be prepared from the sample of (i), (iii) protein- or antibody-containing sample that can be prepared from above tissue, or (iv) peripheral-lymphocyte-containing sample that can be prepared from the above tissue.

The diagnostic method of the present invention can be performed as illustrated below depending on the sample from a living body as a target of measurement.

10-5-1) Method of Measurement Wherein the Target Sample is RNA

When the measurement is directed to RNA, the detection of tumor can be conducted by a process comprising the following steps (a), (b) and (c):

(a) hybridizing RNA prepared from a tissue sample of a test subject or complementary polynucleotide transcribed therefrom to a tumor marker of the present invention (a polynucleotide comprising at least 15 contiguous nucleotides in the base sequence of a polynucleotide of the present invention and/or a polynucleotide complementarily thereto);

b) measuring RNA or a complementary polynucleotide transcribed therefrom hybridized with the tumor marker using as an index said tumor marker; and (c) evaluating whether or not the test subject has a tumor on the basis of measurements in (b).

When the RNA is the target sample of measurement, the present detection method (diagnostic method) can be achieved by detecting and measuring the expression level of PBF gene in the RNA. Specifically, the method can be carried out by a known method such as Northern blotting, RT-PCR, DNA chip analysis, in situ hybridization, or the like using an aforementioned tumor marker of the present invention (a polynucleotide comprising at least 15 contiguous nucleotides in the base sequence of a polynucleotide of the present invention and/or a polynucleotide complementary thereto) as a primer or a probe.

In case of Northern blotting, the tumor marker of the present invention is used as a probe, and the presence/absence or the extent of expression of PBF gene in RNA can be detected and measured. Specifically, the method comprises, for example, labeling a tumor marker (complementary strand) of the present invention with a radioisotope ($^{32}P$, $^{33}P$, etc., RI) or a fluorescent substance, hybridizing the labeled marker to RNA having been prepared from a tissue of a test subject and transferred onto a nylon membrane or the like in a conventional manner, and detecting and measuring the double-strand between the tumor marker (DNA) and RNA on the basis of the signal from the label attached to the tumor marker (RI or fluorescent substance) with a radiation detector (BAS-1800II, Fuji Photo Film., Inc.) or a fluorescence detector. Alternatively, it can be achieved by a method comprising labeling a tumor marker (probe DNA) with AlkPhos Direct Labelling and Detection System (Amersham Pharmacia Biotech) in accordance with the protocol attached thereto; hybridizing the labeled marker to RNA originated from a tissue of a test subject, and detecting and measuring a signal from the label on the tumor marker using Multi-biomeasure STORM860 (Amersham Pharmacia Biotech).

In the case of RT-PCR, tumor marker of the present invention is used as a primer, and the presence/absence or the extent of expression of PBF gene in RNA can be detected and measured expression. Specifically, the method comprises, for example, preparing cDNA from RNA originated from tissue of a test subject in a conventional manner, hybridizing a pair of primers (positive strand hybridizing to the above-mentioned cDNA and reverse strand capable of binding to said +-strand) having been prepared from the tumor marker of the present invention in order to amplify the target region corresponding to PBF gene, conducting PCR in a conventional manner, and detecting the amplified double-stranded DNA. The detection of the amplified double-stranded DNA can be achieved by, for example, a method wherein the PCR is conducted with a primer previously labeled with RI or a fluorescent substance and the resultant labeled double-stranded DNA is detected; a method wherein the resultant double-stranded DNA is transferred onto a nylon membrane or the like, which is then detected by hybridizing with a labeled tumor marker that serves as a probe; or the like. The resultant labeled double stranded DNA products may be measured using Agilent 2100 Bioanalyser (Yokogawa Analytical Systems Inc.) or the like. The measurement may also be achieved by preparing RT-PCR reaction solution using SYBR Green RT-PCR Reagents (Applied Biosystems) according to the protocol attached thereto, conducting the reaction using ABI PRISM 7700 Sequence Detection System (Applied Biosystems), and detecting the reaction products.

In the case of DNA chip analysis, an example of method comprises preparing a DNA chip on which the tumor marker of the present invention used as a DNA probe (single- or double-strand) is attached, hybridizing thereto cRNA having been prepared from RNA originated from tissue of a test subject in a conventional manner, detecting a double stand formed between DNA and cRNA after binding to a labeled probe prepared from the tumor marker of the present invention.

10-5-2) Method of Measurement Wherein the Target Sample is Protein

When the target sample of measurement is protein, the detection method (diagnostic method) of tumor of the present invention can be conducted by a process comprising the following steps (a), (b) and (c):

(a) allowing proteins prepared from a tissue sample of a test subject to bind to a tumor marker of the present invention related to antibody (antibody recognizing PBF);

b) measuring proteins bound to the tumor marker using as an index said tumor marker; and (c) evaluating whether or not the test subject has a tumor on the basis of measurements in (b).

Specifically, the detection method includes a method wherein PBF is detected and measured by a known method such as Western blotting using antibody (antibody recognizing PBF) as a tumor marker of the present invention.

Western blotting can be carried out using, as the primary antibody, a tumor marker, and then, as the second antibody, a labeled antibody (antibody capable of binding to the primary antibody) labeled with a radio isotope (e.g., $^{125}$I, RI), fluorescent substance, enzyme (e.g., horse radish peroxidase, HRP), or the like, and detecting and measuring the signal from RI or fluorescent substance of resultant labeled compounds using radiation detector (BAS-1800II, Fuji Photo Film., Inc., etc), fluorescence detector, or the like. It can also be achieved by a method wherein, after using the tumor marker of the present invention as a primary antibody, the detection is carried out with ECL Plus Western Blotting Detection System (Amersham Pharmacia Biotech & Science) according to the protocol attached thereto, and measurement with Multi-biomeasure STORM860 (Amersham Pharmacia Biotech).

10-5-3) Method of Measurement Wherein the Target Sample is Antibody

When the target sample of measurement is antibody contained in proteins, the detection method (diagnostic method) of tumor of the present invention can be performed by detecting the anti-PBF antibody in a tissue sample of living body, and measuring the quantity thereof. Specifically, it can be carried out in a similar manner to that described in 10-5-2) above using a tumor marker of the present invention related to protein or peptide.

10-5-4) Method of Measurement Wherein the Target Sample is CTL Specific for Tumor Antigen When the target sample of measurement is tumor-antigen-specific CTLs in peripheral blood lymphocytes, the detection method (diagnostic method) of tumor of the present invention can be performed by detecting PBF-specific CTLs in a sample of living body, and measuring the quantity thereof. Specifically, it can be carried out by preparing a tetramer (HLA tetramer) by complexing an HLA antigen fluorescently labeled according to a method described in a literature (Science, 274: p94, 1996) with a peptide of the present invention, and subjecting the tetramer to the detection of CTLs specific for antigen peptides in peripheral blood lymphocytes of a patient suspected to have a tumor using flow cytometry.

10-5-5) Diagnosis of Tumors

Diagnosis of tumor can accomplished by measuring the expression level of PBF gene, quantity of PBF protein that is an expression product of the gene, quantity of anti-PBF antibody, or quantity of PBF-specific CTLs in blood or a tissue suspected to have a tumor of a test subject. Optionally, diagnosis may be carried out by comparing the expression level of said gene or quantity of said protein with that in the corresponding normal tissue.

The comparison of quantity (level) of a gene, protein, antibody or CTL between a tissue of a test subject and the corresponding normal tissue can be carried out by conducting the measurement on the sample from the test subject and that from a normal subject in parallel. When the parallel measurement is not performed, a mean value or statistical intermediate value of the results regarding expression level of PBF gene, quantity of PBF, quantity of anti-PBF antibody or quantity of PBF-specific CTL of a normal subject is used as the value of normal subject, which results have been obtained by conducting measurement under uniform conditions for plural (at least 2, preferably 3, more preferably 5) normal tissues.

Diagnosis whether or not the test subject has a tumor can be carried out on the basis of criterion that the expression level of PBF gene, quantity of PBF, quantity of anti-PBF antibody or quantity of PBF-specific CTL in a tissue of a test subject is at least 2-fold, preferably 3-fold higher compared to that in the corresponding tissue of a normal subject.

EXAMPLES

The present invention is further illustrated by the following examples, but is not limited by these examples in any respect.

Example 1

Establishment of Osteosarcoma Cell Line and Cytotoxic T Lymphocytes (CTLs) Cell Line Thereto A osteosarcoma cell line was established from biopsy osteosarcoma tissue of osteosarcoma patient and named as OS2000. Peripheral-blood mononuclear cells were separated from blood obtained from the same patient by density centrifugation using Lymphoprep (Nycomed), and cultured while stimulating the cells 6 times per every 10 days by adding OS2000 previously inactivated by radiation. CD8-positive cells were then enriched with magnetic beads to which anti-CD8 antibodies are bound (Macs, Miltenyi) and CTL cell lines were established by limiting dilution method (*Int. J. Cancer*, 39, 390-396, 1987, *N. Eng. J. Med*, 333, 1038-1044, 1995). Screening was conducted using as an index the cytotoxic activity on OS2000 to obtain three CTLs. Among them, a CTL named TcOS2000cl-303 was selected and used in the following experiments. It was confirmed that HLA class I molecules for OS2000 include antigens of HLA-A* 2402 -B* 5502, -B40 and Cw1 types.

Example 2

Screening of Gene Encoding Novel Tumor Antigen Protein

1) Screening Using Cells Transformed With HLA-B55 Gene

From OS2000 was prepared mRNA with First track (Invitrogen). A cDNA library was then constructed by preparing a cDNA from the MRNA using Superscript Choice System for cDNA Synthesis (Gibco-BRL) and incorporating into an expression vector pCEP4 (Invitrogen).

On the other hand, HLA-B* 5502 gene (GenBank Acc. No. M77777; *J. Immunol.*, 148(4), 1155-1162 (1992)) isolated from OS2000 cells by PCR was introduced into 293-EBNA cells (Invitrogen) to yield 293-EBNA-B55.

The first screening involved the following procedures. A pool of about 100 cDNA clones (100-200 μg) was introduced into 293-EBNA-B55 cells having been plated into a 96-well microplate at 8×10⁴ cells/well by lipofection method (Lipofectamine 2000, Invitrogen). Pools of respective cDNA clones used for introduction were stored separately. Twenty-four-hour later, TcOS2000cl-303 cells (8×10⁴) were added and cultivation continued for another 24 hours, when the cultured supernatant was recovered. The reactivity of CTL was evaluated by determining LDH released in the supernatant by cytotoxic effects using LDH Cytotoxicity Detection Kit (TAKARA BIO). Among 1000 wells, an well named "IB9" containing the most potent CTL reactivity was selected. Eighty pools of cDNA clones (8-12 cDNA clones/pool) were prepared from 400 cDNAs prepared from the cDNA clone pool that has been used for IB9 gene introduction, and introduced into 293-EBNA-B55 cells in the same manner as the above, and the second screening was conducted using as an index the reactivity of TcOS2000cl-303 cells. As a result, the reactivity was detected in 20 wells. A cDNA clone from the cDNA clone pool in each well of 20 wells was introduced into 293-EBNA-B55 cells in a similar manner to the above and the third screening was conducted using as an index the reactivity of TcOS2000cl-303 cells. As a result, reactivity was detected in 4 wells. The base sequence analysis of each cDNA in 4 wells revealed that these wells contained the same cDNA, which clone was named as IB9.1 H4.

2) Screening Using Cells Transfected With HLA-A24 Gene

In a similar manner to the HLA-B*5502 gene above, an HLA-A* 2402 gene (*Cancer Res.*, 55:4248-4252 (1995), GenBank Accession No. M64740) was introduced into 293-EBNA cells (Invitrogen) to prepare 293-EBNA-A24. Screening was carried out a similar manner to the above where 293-EBNA-B55 cells were used. Thus, the well 2E4 was obtained by the first screening; 22 reactive wells were obtained from the 2E4 by the second screening; and 4 wells were selected by the third screening. The base sequence analysis of cDNA of 4 wells reveled that they contain the same cDNA as cDNA clone 1B9.1H4 that was selected by HLA-B* 5502.

3) Analysis of cDNA Clone 1B9.1H4

Figure 1:
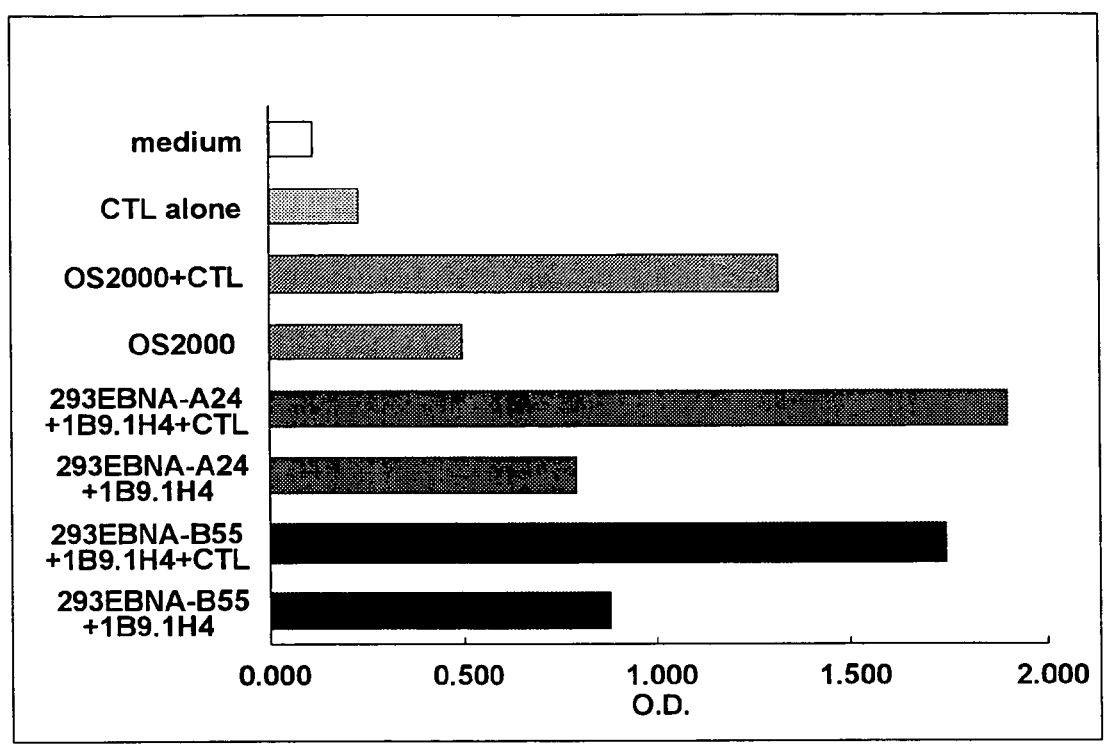
FIG. 1 is a graph showing the reactivity of CTL (TcOS2000cl-303) to EBNA-B55 or 293-EBNA-A24 measured by LDH release assay, wherein the cell was transfected with 1B9.1H4 cDNA and allowed to express the same. In the figure, the abscissa axis represents the absorbance at 490 nm.
Figure 2A:
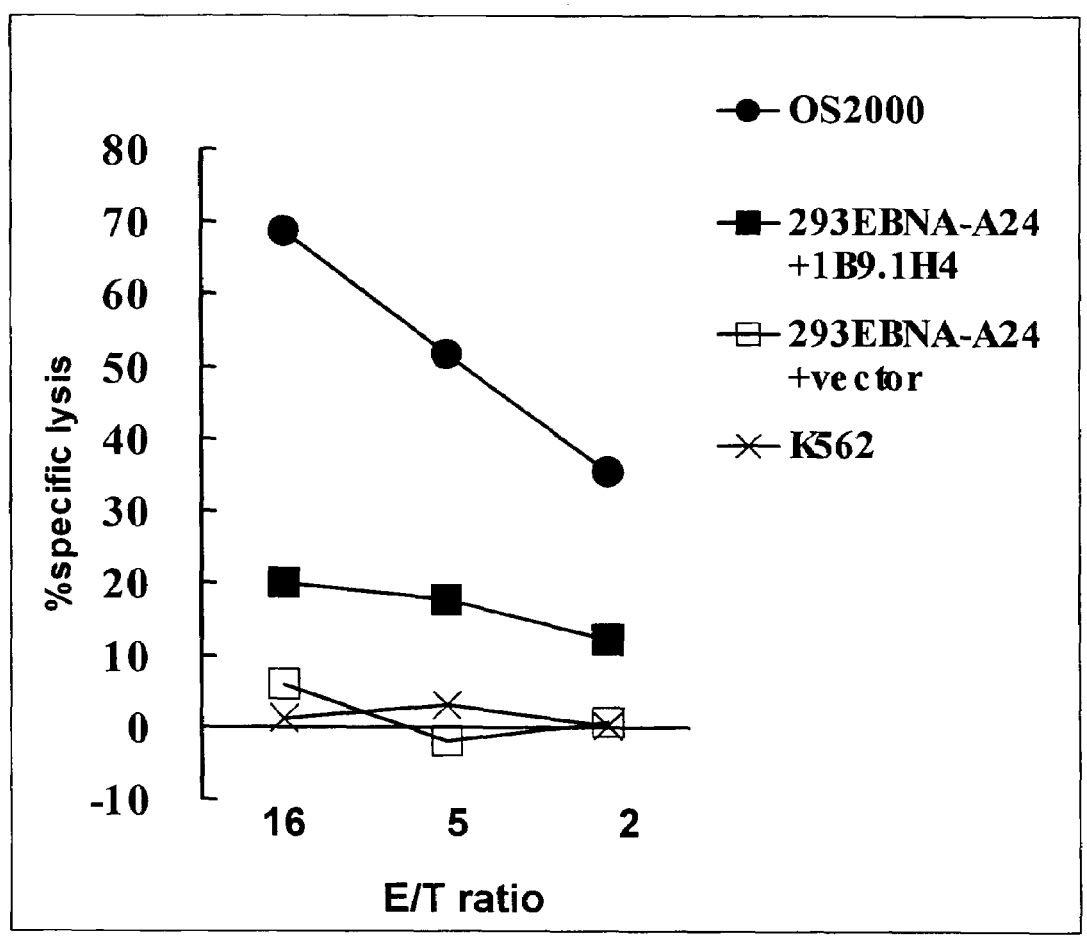
FIG. 2 is a graph showing the reactivity of CTL (TcOS2000cl-303) to EBNA-B55 or 293-EBNA-A24 measured by $^{51}$Cr release assay, wherein the respective cells were transfected with 1B9.1H4 cDNA and allowed to express the same. (A) and (B) show the results obtained using 293-

1B9.1H4 cDNA was introduced into 293-EBNA-B55 or 293-EBNA-A24 and reactivity of TcOS2000cl-303 to the transfected cell expressing the transgene was measured by LDH release assay (determination of released LDH). The results are shown in FIG. 1. The reactivity of TcOS2000cl-303 was also measured by ⁵¹Cr release assay (*J. Immunol.*, 159: 4753, 1997), and the results are shown in FIG. 2 (A, B). TcOS2000cl-303 recognized the cells expressing the introduced cDNA clone 1B9.1H4 and exerted specific cytotoxicity. These results show that cDNA clone 1B9.1H4 encodes a gene of tumor antigen protein that is recognized by TcOS2000cl-303.

Base sequence of cDNA 1B9.1H4 was determined using BigDye Terminator Cycle Sequencing Ready Reaction Kit (Applied Biosystems). The base sequence is shown in SEQ ID NO:3. The full length cDNA was 1901 base pairs in length. The base sequence of SEQ ID NO: 3 was compared with known sequences using publicly available databases and proved to be, for the most part, identical with that of a gene encoding papillomavirus binding factor (PBF), which is also called as papillomavirus regulatory factor (PRF-1) registered as GenBank Accession No. AF263928 (Virology 293, 103-117 (2002)). The base sequence encoding PBF and amino acid sequence corresponding thereto are shown in SEQ ID NO: 1 and 2, respectively.

It was then examined whether or not PBF itself has an activity (reactivity to CTL) as a tumor antigen protein similar to that of aforementioned 1B9.1H4. PBF cDNA was amplified by PCR using cDNA prepared from RNA that has been extracted from OS2000 cells and primers shown in SEQ ID NO: 4 and SEQ ID NO: 5. A PBF gene expression vector constructed by inserting the amplified fragment into expression vector pCEP4 was introduced into the aforementioned 293-EBNA-B55 or 293-EBNA-A24, and reactivity of TcOS2000cl-303 to the transfected cells expressing the transgene was measured by LDH release assay. The results are shown in FIGS. 3 and 4. As is clear from the figures, TcOS2000cl-303 also showed cytotoxic effect on the cells having been transformed with a PBF gene expression vector and expressing the gene. This demonstrated that PBF is a tumor antigen protein that is recognized by TcOS2000cl-303.

Example 3

Identification of Antigen Peptide Binding to HLA-B* 5502

Antigen peptide regions that bind to HLA-B* 5502 was identified from various peptides synthesized on the basis of the amino acid sequence (SEQ ID NO: 2) of tumor antigen protein PBF using as an index the reactivity of TcOS2000cl-303. 293-EBNA-B55A cells (8×10⁴) were pulsed for 1 hour with a peptide having an amino acid sequence (Cys Thr Ala Cys Arg Trp Lys Ala Cys Gln Arg, SEQ ID NO: 46) corresponding to the amino acid sequence at position 499-510 of SEQ ID NO: 2, co-cultured with TcOS2000cl-303 cells (4×10⁴) and the reactivity was assessed by LDH release assay in the same manner as that described in Example 2. The results are shown in FIG. 5. As can be seen, TcOS2000cl-303 cells were not reactive to pepitde-unpulsed 293-EBNA-B55 cells but reacted to peptide-pulsed 293-EBNA-B55 cells, wherein the potpie corresponds to SEQ ID NO: 46. Accordingly, it became clear that the peptide of SEQ ID NO: 46 contains a region capable of binding to HLA-B* 5502.

Example 4

Expression Analysis of PBF Gene in Various Cells and Tissues

The expression of a gene encoding tumor antigen protein PBF in various types of cell and tissue was examined by RT-PCR. cDNA was prepared from RNA extracted from respective cells with Isogen regent (Nippon Gene) using oligo dT primer. PCR was carried out using primers shown in SEQ ID NO: 4 and SEQ ID NO: 5 to amplify PBF cDNA. The PCR products were then separated electrophoretically and analyzed. As a positive control, expression of GPDH gene was examined by RT-PCR method in the same manner above. The results are shown in FIG. 6. Expression of PBF gene was not detected in normal peripheral blood lymphocytes or 293-EBNA cells used for screening, but was confirmed in many cells including OS2000 originated from sarcomas.

Example 5

Expression Analysis of PBF Gene in Renal Cancer Tissue

Expression of a gene encoding tumor antigen protein PBF in renal cancer tissue and normal renal tissue was analyzed using DNA chips. The DNA chip analysis was carried out by a usual method described in WO 03/048359 and the like. As a result, the median expression amount of 91 renal cancer tissues was 780 while that of 67 normal renal tissues was 89, indicating that the expression of PBF gene is increased in renal cancer tissues by about 8.7-fold in a cancer specific manner.

Example 6

Identification of Anti-tumor Peptides Capable of Binding to HLA-A* 2402

A peptide consisting of amino acid sequence shown in SEQ ID NO: 6, 7, 8, 10, 26, 27, 28, 29, 30 or 32 which comprises an HLA-A24 binding motif in the amino acid sequence (SEQ ID NO: 2) of tumor antigen protein PBF was synthesized. Identification of tumor-antigen peptides capable of binding to HLA-A* 2402 was carried out using as an index the reactivity of TcOS2000cl-303. That is, a tumor-antigen peptide capable of binding to HLA-A* 2402 can be identified by co-culturing TcOS2000cl-303 cells with 293-EBNA-A24 cells pulsed with any one of peptides above, and examining the reactivity of CTLs by LDH release assay in a similar manner to Example 2.

INDUSTRIAL APPLICABILITY

The present invention provides use of tumor-antigen protein PBF and a gene encoding the same as an inducer of CTL, or the like. The inducer of CTL of the present invention is useful in treatment of patients suffering from sarcomas or renal cancer.

The invention claimed is:

1. A method for inducing a cytotoxic T cell (CTL) comprising bringing peripheral lymphocyte cells into contact with a peptide that is 8-14 amino acids long and is:
   (i) a fragment of a protein, wherein the protein consists of the amino acid sequence shown in SEQ ID NO: 2; or
   (ii) a fragment of a protein, wherein the protein consists of an amino acid sequence having at least 80% sequence identity to SEQ ID NO: 2,
   wherein the amino acid residue at position 2 of said fragment (ii) is tyrosine, phenylalanine, methionine, or tryptophan, and/or the C terminal amino acid is phenylalanine, leucine, isoleucine, tryptophan, or methionine;

wherein said peptide can bind to an HLA antigen in an HLA-A24 or HLA-B55 restricted manner and is recognized by CTLs when bound to HLA-A24 or HLA-B55 antigen.

2. The method of claim 1 in which the peptide binds to an HLA antigen in a HLA-A24 restricted manner and is recognized by CTLs when bound to an HLA-A24 antigen.

3. The method of claim 1, wherein the peptide is:

(i) a fragment of a protein, wherein the protein consists of the amino acid sequence shown in SEQ ID NO: 2; or (ii) a fragment of a protein, wherein the protein consists of an amino acid sequence having at least 80% sequence identity to SEQ ID NO: 2, and the amino acid residue at position 2 of said fragment (ii) is tyrosine, phenylalanine, methionine, or tryptophan, and the C terminal amino acid is phenylalanine, leucine, isoleucine, tryptophan, or methionine.

4. A peptide which is 8-14 amino acids long, and is:
   (i) a fragment of a protein, wherein the protein consists of the amino acid sequence shown in SEQ ID NO: 2; or
   (ii) a fragment of a protein, wherein the protein consists of an amino acid sequence having at least 80% sequence identity to SEQ ID NO: 2, wherein the amino acid residue at position 2 of said fragment (ii) is tyrosine, phenylalanine, methionine, or tryptophan, and/or the C terminal amino acid is phenylalanine, leucine, isoleucine, tryptophan, or methionine;
   wherein said peptide can bind to an HLA antigen in an HLA-A24 or HLA-B55 restricted manner and is recognized by CTLs when bound to an HLA-A24 or HLA-B55 antigen.

5. The peptide of claim 4, which comprises an amino acid sequence shown in one of SEQ ID NO: 6-46.

6. An epitope peptide consisting essentially of a peptide of claim 4.

7. An inducer of CTL consisting essentially of a peptide of claim 4 as an active ingredient.

8. The peptide of claim 4 that binds to an HLA antigen in a HLA-A24 restricted manner and is recognized by CTLs when bound to an HLA-A24 antigen.

9. The peptide of claim 4 wherein the amino acid residue at position 2 of said fragment (ii) is tyrosine, phenylalanine, methionine, or tryptophan, and the C terminal amino acid is phenylalanine, leucine, isoleucine, tryptophan, or methionine.

10. The peptide of claim 5 that consists of an amino acid sequence of one of SEQ ID NO: 6-46.

11. The peptide of claim 5 that consists of the amino acid sequence of SEQ ID NO: 6.

12. A method for producing an antigen-presenting cell comprising the step of bringing a cell having antigen-presenting ability into contact with a peptide which is 8-14 amino acids long and is
   (i) a fragment of a protein, wherein the protein consists of the amino acid sequence shown in SEQ ID NO: 2; or
   (ii) a fragment of a protein, wherein the protein consists of an amino acid sequence having at least 80% sequence identity to SEQ ID NO: 2
   wherein the amino acid residue at position 2 of said fragment (ii) is tyrosine, phenylalanine, methionine, or tryptophan, and/or the C terminal amino acid is phenylalanine, leucine, isoleucine, tryptophan, or methionine;
   wherein said peptide can bind to an HLA antigen in an HLA-A24 or HLA-B55 restricted manner and is recognized by CTLs when bound to an HLA-A24 or HLA-B55 antigen.

13. The method of claim 12 in which the peptide binds to an HLA antigen in a HLA-A24 restricted manner and is recognized by CTLs when bound to an HLA-A24 antigen.

14. The method of claim 12, wherein the peptide is:
   (i) a fragment of a protein, wherein the protein consists of the amino acid sequence shown in SEQ ID NO: 2; or
   (ii) a fragment of a protein, wherein the protein consists of an amino acid sequence having at least 80% sequence identity to SEQ ID NO: 2, and the amino acid residue at position 2 of said fragment (ii) is tyrosine, phenylalanine, methionine, or tryptophan, and the C terminal amino acid is phenylalanine, leucine, isoleucine, tryptophan, or methionine.

15. A tumor marker consisting essentially of a peptide as set forth in claim 4.

16. The tumor marker of claim 15, which comprises at least 8 contiguous amino acids in the amino acid sequence shown in SEQ ID NO: 2.

17. The tumor marker of claim 15, wherein the tumor is sarcoma or renal cancer.

18. A diagnostic agent for tumor consisting essentially of a tumor marker of claim 15.

* * * * *